United States Patent
Luo et al.

(10) Patent No.: US 11,918,709 B2
(45) Date of Patent: Mar. 5, 2024

(54) MEDICAL DEVICE COMPRISING COVALENTLY BONDED HEPARIN COATING

(71) Applicant: Medtech Coating Technologies Pte Ltd, Singapore (SG)

(72) Inventors: He-Kuan Luo, Singapore (SG); Honglei Wang, Singapore (SG); Chung Yen Ang, Singapore (SG)

(73) Assignee: jMedtech Coating Technologies Pte Ltd, Singapore (SG)

( * ) Notice: Subject to any disclaimer, the term of this patent is extended or adjusted under 35 U.S.C. 154(b) by 147 days.

(21) Appl. No.: 17/440,510

(22) PCT Filed: Mar. 19, 2020

(86) PCT No.: PCT/SG2020/050146
§ 371 (c)(1),
(2) Date: Sep. 17, 2021

(87) PCT Pub. No.: WO2020/190214
PCT Pub. Date: Sep. 24, 2020

(65) Prior Publication Data
US 2022/0152281 A1    May 19, 2022

Related U.S. Application Data

(60) Provisional application No. 62/820,556, filed on Mar. 19, 2019.

(51) Int. Cl.
*A61L 33/00* (2006.01)
*A61L 27/18* (2006.01)
(Continued)

(52) U.S. Cl.
CPC ........... *A61L 33/0011* (2013.01); *A61L 27/18* (2013.01); *A61L 27/34* (2013.01); *A61L 27/54* (2013.01);
(Continued)

(58) Field of Classification Search
CPC .................................................. A61L 33/0011
See application file for complete search history.

(56) References Cited

U.S. PATENT DOCUMENTS 6,953,625 B2    10/2005    Koulik
8,101,196 B2    1/2012    Luthra et al.
(Continued)

FOREIGN PATENT DOCUMENTS

EP    1462127 A1    9/2004
WO    2001/039814 A1    6/2001
(Continued)

OTHER PUBLICATIONS

Brunelli, Nicholas A. et al. "Catalytic Regioselective Epoxide Ring Opening with Phenol Using Homogeneous and Supported Analogues of Dimethylaminopyridine" Top Catal (2012) 55:432-438 (7 pages).
(Continued)

*Primary Examiner* — Dah-Wei D. Yuan
*Assistant Examiner* — Andrew J Bowman
(74) *Attorney, Agent, or Firm* — Osha Bergman Watanabe & Burton LLP

(57) ABSTRACT

Disclosed herein is a medical device, comprising a covalently-bonded heparin coating on a substrate, where the covalently bonded heparin coating is the reaction product of (a) an isocyanate-bearing material on or covalently bonded to the substrate and (b) a heparin molecule selected from one of the formulae in the claims. The current invention also relates to a method of forming the medical device, which may be useful as heart stent or intravascular stent that is hemocompatible for preventing the formation of blood clots.

19 Claims, 5 Drawing Sheets

(51) Int. Cl.
    *A61L 27/34*     (2006.01)
    *A61L 27/54*     (2006.01)
    *A61L 29/06*     (2006.01)
    *A61L 29/08*     (2006.01)
    *A61L 29/16*     (2006.01)
    *A61L 31/06*     (2006.01)
    *A61L 31/10*     (2006.01)
    *A61L 31/16*     (2006.01)

(52) U.S. Cl.
    CPC ............. *A61L 29/06* (2013.01); *A61L 29/085* (2013.01); *A61L 29/16* (2013.01); *A61L 31/06* (2013.01); *A61L 31/10* (2013.01); *A61L 31/16* (2013.01); *A61L 2300/42* (2013.01); *A61L 2420/02* (2013.01)

(56) References Cited

U.S. PATENT DOCUMENTS

| | | |
|---|---|---|
| 8,501,212 B2 | 8/2013 | Vestberg |
| 8,608,899 B2 | 12/2013 | Kramer et al. |
| 2004/0005470 A1 | 1/2004 | Koulik |
| 2004/0142016 A1 | 7/2004 | Luthra et al. |
| 2011/0274821 A1 | 11/2011 | Luthra et al. |
| 2015/0352265 A1 | 12/2015 | Garimella et al. |

FOREIGN PATENT DOCUMENTS

| | | | |
|---|---|---|---|
| WO | 2005118018 A1 | 12/2005 | |
| WO | WO-2005118018 A1 * | 12/2005 | ............. A61L 31/10 |

OTHER PUBLICATIONS

Parker, R. E. et al. "Mechanisms of Epoxide Reactions" Department of Chemistry, The University, Southampton, England and National Research Council, Ottawa 8, Canada Received Apr. 17, 1959 pp. 737-799 (63 pages).

Nie, Jing-Jun et al. "Controllable Heparin-Based Comb Copolymers and Their Self-Assembled Nanoparticles for Gene Delivery" ACS Appl. Mater. Interfaces, Mar. 7, 2016 (41 pages).

International Search Report issued in International Application No. PCT/SG2020/050146 dated Jul. 8, 2020 (4 pages).

Written Opinion issued in International Application No. PCT/SG2020/050146 dated Jul. 8, 2020 (5 pages).

Biran, R. et al. "Heparin coatings for improving blood compatibility of medical devices" Advanced Drug Delivery Reviews 112 (2017) 12-23 (12 pages).

* cited by examiner (a)

(b)

MEDICAL DEVICE COMPRISING COVALENTLY BONDED HEPARIN COATING

FIELD OF INVENTION

The current invention relates to a medical device. In particular, the medical device may comprise a covalently-bonded heparin coating on a substrate (for example, a polyurethane tube).

BACKGROUND

The listing or discussion of a prior-published document in this specification should not necessarily be taken as an acknowledgement that the document is part of the state of the art or is common general knowledge.

Heparin is one of the most effective anticoagulant agents which is widely used in antithrombogenic coatings on medical devices (such as synthetic polymer devices). Such coating provides an antithrombotic effect on the device to prevent the formation of blood clots, which is required when these devices are used as heart stents or intravascular stents or organ supports, or used in blood collection and separation applications (*Advanced Drug Delivery Reviews* 2017, 112, 12-23; U.S. Pat. Nos. 8,501,212; 6,953,625; 8,101,196; US 2004/0142016; US 2011/0274821; WO 2001/039814). Typically, such heparin coatings have to be covalently bonded on the surface of the devices so that the heparin coatings could last longer in the human body, as well as to avoid the health risks caused by the heparin that leached into the blood from the surface of the devices.

Existing coating techniques involve creating aldehyde groups (as active sites) on heparin by oxidation reactions (such as using nitrous acid or $KIO_4$), followed by Schiff-Base condensation with amines, reduction with $NaCNBH_3$ and more steps such as thiol-ene click reaction (U.S. Pat. No. 8,501,212), or forming a heparin-polyoxyalkylenepolyamine adduct (U.S. Pat. No. 6,953,625). However, the oxidation reaction destroys part of the heparin structure, which inevitably decreases the antithrombogenic capability of heparin. Furthermore, the multi-step coating route is time-consuming and costly.

In U.S. Pat. No. 8,101,196, an aqueous solution of benzalkonium chloride was added to an aqueous solution of heparin sodium to prepare a non-water soluble heparin-benzalkonium complex. The heparin-benzalkonium complex is soluble in dichloromethane (DCM), allowing the hydroxyl groups of heparin to react with methacryloyl chloride to attach carbon double bonds on the heparin backbone, followed by steps (such as polymerisation) to fabricate a heparin-containing gel on medical devices. However, all the reactions were carried out in THF or DCM, which are not compatible with some polymer devices, especially polyurethane devices because they can be deformed by THF or DCM solvents.

US 2015/0352265 discloses a method to make a heparin-containing coating on a surface of an oxygenator device [e.g., a Hollow Fiber Membrane (HFM) surface]. Apart from heparin, the coating comprises polyvinylpyrrolidone (PVP) and quaternary aliphatic alkylammonium chloride (or bromide) having at least one radical being a plain or substituted long-chain aliphatic group from $C_7H_{15}$ to $C_{18}H_{37}$. As an alcohol (such as methanol) was used as co-solvent with other organic solvents (such as THF), the hydroxyl groups of heparin cannot be used for covalent bonding to the device. In any case, covalent bonding was not mentioned in the method of the patent.

In addition, the most commonly available form of heparin is heparin sodium, which is only soluble in water. This poses limitations to coating heparin sodium onto the medical devices because, in the aqueous solution of heparin sodium, a compound (such as acryloyl chloride) that reacts with the hydroxyl groups of heparin, can also react with water molecules. Thus the hydroxyl groups of heparin cannot be used as active sites for covalent coating in aqueous solution.

Given the above, the choice of solvent is important to allow heparin to be covalently coated on medical devices. The solvent should fully dissolve heparin to facilitate the covalent bonding reactions. In addition, the solvent should not deform the polymer device, and the chemical reaction should not destroy part of the heparin structure.

Therefore, there is need to develop a better coating method that allows heparin to be covalently coated on medical devices easily and effectively. More importantly, the method must be able to produce heparin coatings that are long-lasting and does not degrade heparin in the coating process (for example, by utilising the existing hydroxyl groups in heparin for bonding to the device). Furthermore, the method should involve as few steps as possible and take place in a solvent that is compatible with all polymer devices (especially polyurethane), such as acetonitrile.

SUMMARY OF INVENTION

Various aspects and embodiments of the invention are disclosed by reference to the following numbered clauses.

1. A medical device, comprising a covalently-bonded heparin coating on a substrate, where the covalently bonded heparin coating is the reaction product of:
   (a) an isocyanate-bearing material on or covalently bonded to the substrate, which isocyanate-bearing material comprises one or more isocyanate groups; and
   (b) a heparin molecule selected from one or more of the following formulae:

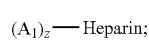

Ia

Ib

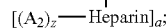

and

Ic: $\{([HS(CH_2)_n]_m\text{-}L_2\text{-}[(CH_2)_nS(CH_2)_oO])_z\text{-}Heparin\}_p$, where the oxygen atom bonded to Heparin is part of the Heparin molecule;

Id: $\{([HS(CH_2)_n]_m\text{-}L_3\text{-}[(CH_2)_nS(CH_2)_oCOO])_z\text{-}Heparin\}_{p'}$, where the oxygen atom bonded to Heparin is part of the Heparin molecule;

Ie: $\{([HS(CH_2)_{n''}]_{m''}\text{-}L_4\text{-}[(CH_2)_nS(C_qH_{2q-2})O])_z\text{-}Heparin\}_{p''}$, where the oxygen atom bonded to Heparin is part of the Heparin molecule; and If: a network of heparin molecules comprising fixing portions of formula Ifi:

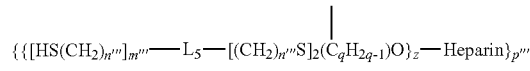

where the oxygen atom bonded to Heparin is part of the Heparin molecule; and network extending portions of formula Ifii:

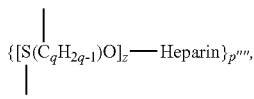

where the oxygen atom bonded to Heparin is part of the Heparin molecule;
where:
each $A_1$ and $A_2$ independently represent:
HO—;
$H(OCHR_1CH_2)_xO$—, where the terminal oxygen atom is part of the Heparin molecule; or
$H(OCHR_1CHR_2)_xO$—, where $R_1$ and $R_2$, together with the atoms they are attached to, form a carbocylic ring system having from 3 to 10 carbon atoms;
$L_1$ represents a crosslinking moiety;
a represents 1 to 25;
each z independently represents 1 to 50;
each n, n', n", n''', o and o' independently represent 1 to 20;
each m, m', m", m''', p, p', p", p''' and p'''' independently represent 1 to 20;
each q independently represents 1 to 20;
each $L_2$ to $L_5$ each independently represent a linking group;
$R_1$ represents H or a $C_1$ to $C_{20}$ alkyl group;
x represents from 1 to 20;
| in formula Ib represents a covalent bond between a Heparin molecule and the crosslinking moiety;
each | in formula Ifi represents a point of attachment to a further fixing portion of formula Ifi or to an extending portion of formula Ifii;
each | in formula Ifii represents a point of attachment to a fixing portion of formula Ifi or to a further extending portion of formula Ifii;
each Heparin molecule is a polyanionic molecule, where each negative charge is balanced by a cation, wherein:
the cations are substantially quaternary ammonium ions; and
the isocyanate-bearing material is a coating on the substrate or is covalently bonded to the substrate.

2. The medical device according to Clause 1, wherein in the compound of formula Ib, a represents 1 to 10, such as from 2 to 5, such as from 3 to 4.

3. The medical device according to Clause 1, wherein in the compounds of formula Ic to If each n, n', n", n''' independently represent 1 to 25, such as from 2 to 10, such as from 3 to 5.

4. The medical device according to Clause 1 or Clause 3, wherein in the compounds of formula Ic to If:
(a) each m, m', m", m''', p, p', p", p''' and p'''' independently represent 1 to 10, such as 1 to 3; and/or
(b) each q independently represents 1 to 15, such as 1 to 10, such as 1 to 6.

5. The medical device according to any one of Clauses 1, and 3 to 4, wherein in the compounds of formula Ic to If:
(a) each $L_2$ to $L_5$ each independently represent a linking group in the form of a branched or unbranched $C_{1-10}$ alkyl chain, which alkyl chain is unsubstituted or substituted by one or more groups selected from $C_{1-6}$ alkyl. O or N, or which alkyl chain may be interrupted by a heteroatom (such as O, N); and/or
(b) each o and o' independently represents 1 to 10, such as 1 to 2.

6. The medical device according to Clause 1, wherein in the compounds of formula Ia and Ib, each $R_1$ represents H or a $C_1$ to $C_5$ alkyl group.

7. The medical device according to Clause 1 or Clause 6, wherein in the compound of formula Ib:
(a) $L_1$ is a crosslinking moiety derived from one or more of the group consisting of a linear or branched di-acid chloride, a linear or branched tri-acid chloride, a linear or branched di-epoxide, a linear or branched tri-epoxide, and a linear or branched tetrakis-epoxide, optionally wherein the crosslinking moiety is derived from a compound selected from one or more of the group consisting of adipoyl chloride, dodececanedioyl dichloride, sebacoyl dichloride, suberoyl dichloride, 1,2-butanediol diglycidyl ether, neopentyl glycol diglycidyl ether, and trimethylolpropane triglycidyl ether; and/or
(b) x represents 1 to 10, such as 1 to 5.

8. The medical device according to any one of the preceding clauses, wherein the cations are substantially $C_{1-30}$ alkyl quaternary ammonium ions, such as $C_{1-10}$ alkyl quaternary ammonium ions, such as tetrabutyl ammonium ions.

9. The medical device according to any one of the preceding clauses, wherein the isocyanate-bearing material is covalently bonded to the substrate, optionally wherein the isocyanate-bearing material covalently bonded to the substrate is derived from one or more of hexamethylene diisocyanate, poly(hexamethylene diisocyanate), 4,4'-methylenebis(phenyl isocyanate), and trans-1,4-cyclohexylene diisocyanate.

10. The medical device according to any one of the preceding clauses, wherein the substrate is a polymer, a ceramic or a metal, optionally wherein the substrate is a polymer selected from one or more of the group consisting of a polyurethane, PTFE, polyethylene and PVC (e.g. the substrate is a polyurethane).

11. A method of forming a medical device as described in any one of Clauses 1 to 10, the method comprising the steps of:
(a) providing an isocyanate-bearing material on or covalently bonded to a substrate, which isocyanate-bearing material comprises one or more isocyanate groups;
(b) reacting the isocyanate-bearing material on or covalently bonded to the substrate in a polar aprotic solvent with a heparin molecule selected from one or more of the following formulae:

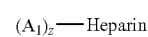

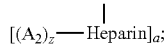

and
Ic: $\{([HS(CH_2)_n]_m\text{-}L_2\text{-}[(CH_2)_nS(CH_2)_oO])_z\text{-Heparin}\}_p$, where the oxygen atom bonded to Heparin is part of the Heparin molecule;
Id: $\{([HS(CH_2)_n]_m\text{-}L_3\text{-}[(CH_2)_nS(CH_2)_oCOO])_z\text{-Heparin}\}_{p'}$, where the oxygen atom bonded to Heparin is part of the Heparin molecule;

Ie: $\{([HS(CH_2)_{n''}]_{m''}-L_4-[(CH_2)_{n''}S(C_qH_{2q-2})O])_z-$ Heparin$\}_{p'''}$, where the oxygen atom bonded to Heparin is part of the Heparin molecule; and If: a network of heparin molecules comprising fixing portions of formula Ifi:

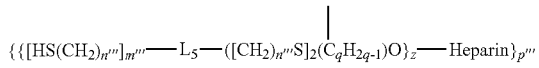

where the oxygen atom bonded to Heparin is part of the Heparin molecule; and network extending portions of formula Ifii:

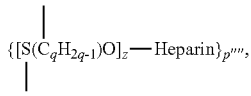

where the oxygen atom bonded to Heparin is part of the Heparin molecule;

to provide the medical device described in any one of Clauses 1 to 10, where: each $A_1$ and $A_2$ independently represent:

HO—;

$H(OCHR_1CH_2)_xO$—, where the terminal oxygen atom is part of the Heparin molecule; or $H(OCHR_1CHR_2)_xO$—, where $R_1$ and $R_2$, together with the atoms they are attached to, form a carbocylic ring system having from 3 to 10 carbon atoms;

$L_1$ represents a crosslinking moiety;

a represents 1 to 25;

each z independently represents 1 to 50;

each n, n', n'', n''', o and o' independently represent 1 to 20;

each m, m', m'', m''', p, p', p'', p''' and p'''' independently represent 1 to 20;

each q independently represents 1 to 20;

each $L_2$ to $L_5$ each independently represent a linking group;

$R_1$ represents H or a $C_1$ to $C_{20}$ alkyl group;

x represents from 1 to 20;

| in formula Ib represents a covalent bond between a Heparin molecule and the crosslinking moiety;

each | in formula Ifi represents a point of attachment to a further fixing portion of formula Ifi or to an extending portion of formula Ifii;

each | in formula Ifii represents a point of attachment to a fixing portion of formula Ifi or to a further extending portion of formula Ifii;

each Heparin molecule is a polyanionic molecule, where each negative charge is balanced by a cation, wherein:

the cations are substantially quaternary ammonium ions; and the isocyanate-bearing material is a coating on the substrate or is covalently bonded to the substrate.

12. The method according to Clause 11, wherein in the compound of formula Ib, a represents 1 to 10, such as from 2 to 5, such as from 3 to 4.

13. The method according to Clause 11, wherein in the compounds of formula Ic to If each n, n', n'', n''' independently represent 1 to 25, such as from 2 to 10, such as from 3 to 5.

14. The method according to Clause 11 or Clause 13, wherein in the compounds of formula Ic to If:

(a) each m, m', m'', m''', p, p', p'', p''' and p'''' independently represent 1 to 10, such as 1 to 2; and/or (b) each q independently represents 1 to 15, such as 1 to 10, such as 1 to 6.

15. The method according to any one of Clauses 11, and 13 to 14, wherein in the compounds of formula Ic to If:

(a) each $L_2$ to $L_5$ each independently represent a linking group in the form of a branched or unbranched $C_{1-10}$ alkyl chain, which alkyl chain is unsubstituted or substituted by one or more groups selected from $C_{1-6}$ alkyl. O or N, or which alkyl chain may be interrupted by a heteroatom (such as O, N); and/or (b) each o and o' independently represents 1 to 10, such as 1 to 2.

16. The method according to Clause 11, wherein in the compounds of formula Ia and Ib, each $R_1$ represents H or a $C_1$ to $C_5$ alkyl group.

17. The method according to Clause 11 or Clause 16, wherein in the compound of formula Ib:

(a) $L_1$ is a crosslinking moiety derived from one or more of the group consisting of a linear or branched di-acid chloride, a linear or branched tri-acid chloride, a linear or branched di-epoxide, a linear or branched tri-epoxide, and a linear or branched tetrakis-epoxide, optionally wherein the crosslinking moiety is derived from a compound selected from one or more of the group consisting of adipoyl chloride, dodececanedioyl dichloride, sebacoyl dichloride, suberoyl dichloride, 1,2-butanediol diglycidyl ether, neopentyl glycol diglycidyl ether, and trimethylolpropane triglycidyl ether; and/or (b) x represents 1 to 10, such as 1 to 5.

18. The method according to any one of Clauses 11 to 17, wherein the cations are substantially $C_{1-30}$ alkyl quaternary ammonium ions, such as $C_{1-10}$ alkyl quaternary ammonium ions, such as tetrabutyl ammonium ions.

19. The method according to any one of Clauses 11 to 18, wherein the isocyanate-bearing material is covalently bonded to the substrate, optionally wherein the isocyanate-bearing material covalently bonded to the substrate is derived from one or more of hexamethylene diisocyanate, poly(hexamethylene diisocyanate), 4,4'-methylenebis(phenyl isocyanate), and trans-1,4-cyclohexylene diisocyanate.

20. The method according to any one of Clauses 11 to 19, wherein the substrate is a polymer, a ceramic or a metal, optionally wherein the substrate is a polymer selected from one or more of the group consisting of a polyurethane, PTFE, polyethylene and PVC (e.g. the substrate is a polyurethane).

21. The method according to any one of Clauses 11 to 19, wherein the polar aprotic solvent is acetonitrile.

22. The method according to Clause 11, wherein when $A_1$ in the compound of formula Ia or $A_1$ and/or $A_2$ in the compound of formula Ib is $H(OCHR_1CH_2)_xO$— or $H(OCHR_1CHR_2)_xO$—, the compound of formula Ia or Ib is formed by reacting heparin with an epoxide.

23. The method according to Clause 11, wherein the crosslinks between the heparin molecules in the compound of formula Ib are formed by providing $(A_1)_z$-Heparin and $(A_2)_z$-Heparin, where $A_1$, $A_2$ and z are as defined in Clause 11, and reacting these compounds with a crosslinking agent, optionally wherein the crosslinking agent is selected from one or more of the group consisting of a linear or branched di-acid chloride, a linear or branched tri-acid chloride, a linear or branched di-epoxide, a linear or branched tri-epoxide, and a linear or branched tetrakis-epoxide (e.g. the crosslinking moiety is selected from one or more of the group consisting of adipoyl chloride, dodececanedioyl dichloride, sebacoyl dichloride, suberoyl dichloride, 1,2-butanediol diglycidyl ether, neopentyl glycol diglycidyl ether, and trimethylolpropane triglycidyl ether).

24. The method according to Clause 11, wherein the compound of formula If is prepared by reacting a heparin molecule modified to present one or more carbon to carbon double bond functional groups or carbon to carbon triple bond functional groups with a compound comprising multiple thiol groups, optionally wherein the compound comprising multiple thiol groups is selected from the group consisting of pentaerythritol tetrakis(3-mercaptopropionate), trimethylolpropane tris(3-mercaptopropionate), and 2,2'-(ethylenedioxy)diethanethiol.

25. The method according to Clause 24, wherein the heparin molecule modified to present one or more carbon to carbon double bond functional groups or carbon to carbon triple bond functional groups is prepared by reacting heparin with:

(a) a compound of formula IIa:

$$H_2C=C-(CH_2)_k-XX \quad \text{IIa,}$$

where k is from 1 to 50 and XX is halo (e.g. the compound of formula IIa is allyl bromide); or (b) a compound of formula IIb:

$$HC\equiv C-(CH_2)_{k'}-XX \quad \text{IIb,}$$

where k' is from 1 to 50 and XX is halo (e.g. the compound of formula IIb is propargyl bromide); or (c) a compound of formula IIc:

$$XX-C(O)-R_2 \quad \text{IIc,}$$

where XX is halo and $R_2$ is $C_{1-50}$ alkyl (e.g. the compound of formula IIc is selected from one or more of the group consisting of 10-undecenoyl chloride, 4-pentenoyl chloride, and acryloyl chloride).

26. A medical device as described in any one of Clauses 1 to 10 for use as heart stent or intravascular stent that is hemocompatible for preventing the formation of blood clots.

27. A medical device as described in any one of Clauses 1 to 10 for use as organ support that is hemocompatible for preventing the formation of blood clots.

28. A medical device as described in any one of Clauses 1 to 10 for use in blood collection and separation.

29. A medical device as described in any one of Clauses 1 to 10 for use in preventing blood clots.

DESCRIPTION

Figure 1:
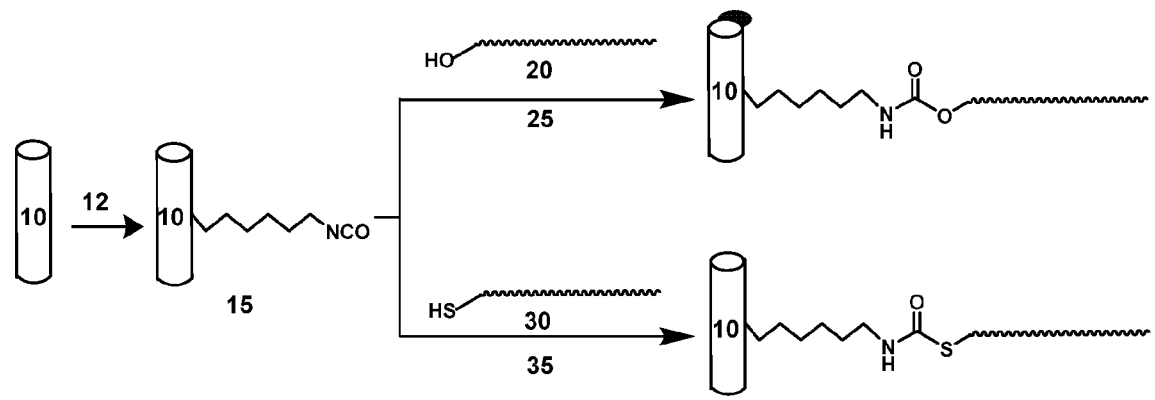
FIG. 1 depicts a schematic representation of the current invention to prepare heparin-coated medical device via reacting an isocyanate-coated polyurethane device (15) with modified or unmodified heparin-tetrabutylammonium (TBA) (20 or 30) via: (a) the carbamate-forming reaction in acetonitrile (25); or (b) the thiol-isocyanate click reaction in acetonitrile (35).

It has been surprisingly found that more effective heparin coatings can be obtained by covalently bonding heparin to a substrate through the covalent bond forming reaction between isocyanates and heparin itself or functionalised heparin molecules. An important feature of this process (and resulting products) is the use of heparin molecules where the counter cations to the negative charges on heparin are quaternary ammonium cations. It has been surprisingly found that the use of these species allows the use of a wider range of solvents that are compatible with polymeric materials that may be particularly suitable as substrates. Thus, there is disclosed a medical device, comprising a covalently-bonded heparin coating on a substrate, where the covalently bonded heparin coating is the reaction product of:

(a) an isocyanate-bearing material on or covalently bonded to the substrate, which isocyanate-bearing material comprises one or more isocyanate groups; and (b) a heparin molecule selected from one or more of the following formulae:

$$(A_1)_z-\text{Heparin}; \quad \text{Ia}$$

$$\begin{array}{c}(A_1)_z-\text{Heparin}\\|\\L_1\\|\\ [(A_2)_z-\text{Heparin}]_a;\end{array} \quad \text{Ib}$$

and

Ic: $\{([HS(CH_2)_n]_m\text{-}L_2\text{-}[(CH_2)_nS(CH_2)_oO])_z\text{-Heparin}\}_p$, where the oxygen atom bonded to Heparin is part of the Heparin molecule;

Id: $\{([HS(CH_2)_n]_m\text{-}L_3\text{-}[(CH_2)_nS(CH_2)_oCOO])_z\text{-}$Heparin$\}_p$, where the oxygen atom bonded to Heparin is part of the Heparin molecule;

Ie: $\{([HS(CH_2)_{n''}]_{m'''}\text{-}L_4\text{-}[(CH_2)_{n''}S(C_qH_{2q-2})O])_z\text{-}Heparin\}_{p'''}$, where the oxygen atom bonded to Heparin is part of the Heparin molecule; and If: a network of heparin molecules comprising fixing portions of formula Ifi:

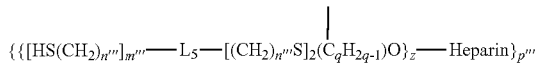

where the oxygen atom bonded to Heparin is part of the Heparin molecule; and
network extending portions of formula Ifii:

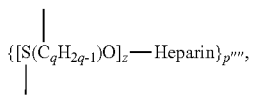

where the oxygen atom bonded to Heparin is part of the Heparin molecule;
where:
each $A_1$ and $A_2$ independently represent:
HO—;
$H(OCHR_1CH_2)_xO$—, where the terminal oxygen atom is part of the Heparin molecule; or
$H(OCHR_1CHR_2)_xO$—, where $R_1$ and $R_2$, together with the atoms they are attached to, form a carbocylic ring system having from 3 to 10 carbon atoms;
$L_1$ represents a crosslinking moiety;
a represents 1 to 25;
each z independently represents 1 to 50;
each n, n', n'', n''', o and o' independently represent 1 to 20;
each m, m', m'', m''', p, p', p'', p''' and p'''' independently represent 1 to 20;
each q independently represents 1 to 20;
each $L_2$ to $L_5$ each independently represent a linking group;
$R_1$ represents H or a $C_1$ to $C_{20}$ alkyl group;
x represents from 1 to 20;
| in formula Ib represents a covalent bond between a Heparin molecule and the crosslinking moiety;
each | in formula Ifi represents a point of attachment to a further fixing portion of formula Ifi or to an extending portion of formula Ifii;
each | in formula Ifii represents a point of attachment to a fixing portion of formula Ifi or to a further extending portion of formula Ifii;
each Heparin molecule is a polyanionic molecule, where each negative charge is balanced by a cation, wherein:
the cations are substantially quaternary ammonium ions; and
the isocyanate-bearing material is a coating on the substrate or is covalently bonded to the substrate.

In embodiments herein, the word "comprising" may be interpreted as requiring the features mentioned, but not limiting the presence of other features. Alternatively, the word "comprising" may also relate to the situation where only the components/features listed are intended to be present (e.g. the word "comprising" may be replaced by the phrases "consists of" or "consists essentially of"). It is explicitly contemplated that both the broader and narrower interpretations can be applied to all aspects and embodiments of the present invention. In other words, the word "comprising" and synonyms thereof may be replaced by the phrase "consisting of" or the phrase "consists essentially of" or synonyms thereof and vice versa.

Figure 2:
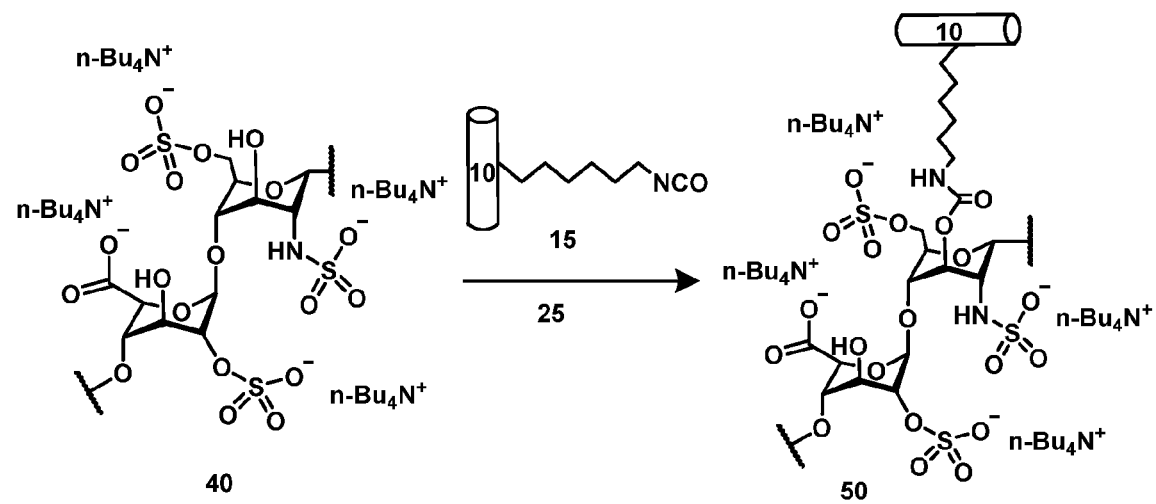
FIG. 2 depicts a schematic representation of coating heparin-TBA (40) on PHMDI- or HDI-coated PU tube (15) via the carbamate-forming reaction in acetonitrile (25), to give the heparin-coated PU tube (50) of the current invention.

Heparin is a sulfated polysaccharide which consists largely of an alternating sequence of hexuronic acid and 2-amino-2-deoxy-D-glucose. The repeating unit of heparin is depicted in FIG. 2. Heparin is readily available in an unfractionated form, which may contain molecules with a wide range of molecular weights. Commercially-available heparin can typically contain a range of heparin chains with molecular weights ranging from 1,000 Daltons or less to 50,000 Daltons or more. Examples of heparin that may be used in the current invention may have a molecular weight of from 3,000 to 30,000 Daltons. The heparins used in the current invention are ones in which the cation that counterbalances the anions (—COO⁻ and —$SO_3^-$) on the heparin backbone are substantially quaternary ammonium cations and, more particularly, they are quaternary alkyl ammonium cations.

A general overview of the process to produce the coated heparin medical devices is provided by FIG. 1. In the first instance, a substrate 10 is reacted or coated with a material 12 (not depicted) to provide an isocyanate-bearing substrate 15. As will be appreciated, for the purposes of clarity only one isocyanate-bearing group is depicted, but there will be multiple isocyanate-bearing groups on the surface of the substrate. The isocyanate molecule may be covalently bonded to the surface of the substrate (e.g. using a diisocyanate molecule that reacts with the surface of the substrate) or it may be coated thereon. The isocyanate-bearing substrate 15 may then be reacted with a hydroxyl-bearing heparin 20 (the hydroxyl group may be one directly on the backbone of heparin, or be one that is spaced apart from the heparin backbone by a linking group) or a thiol-bearing heparin 30, which thiol group is spaced apart from the heparin backbone by a linking group.

Any suitable substrate material may be used, such as ceramics, metals or, more particularly, synthetic polymers. Suitable synthetic polymers that may be mentioned herein include, but are not limited to polyurethane, PTFE, polyethylene or PVC. In particular embodiments of the invention, the substrate may be a polyurethane. In embodiments of the invention that may be mentioned herein, the isocyanate-bearing material may be covalently bonded to the substrate. In embodiments where the isocyanate-bearing material is covalently bonded to the substrate, the resulting covalently bonded isocyanate may be derived from one or more of a group including, but not limited to, hexamethylene diisocyanate, poly(hexamethylene diisocyanate), 4,4'-methylenebis(phenyl isocyanate), and trans-1,4-cyclohexylene diisocyanate.

Figure 3:
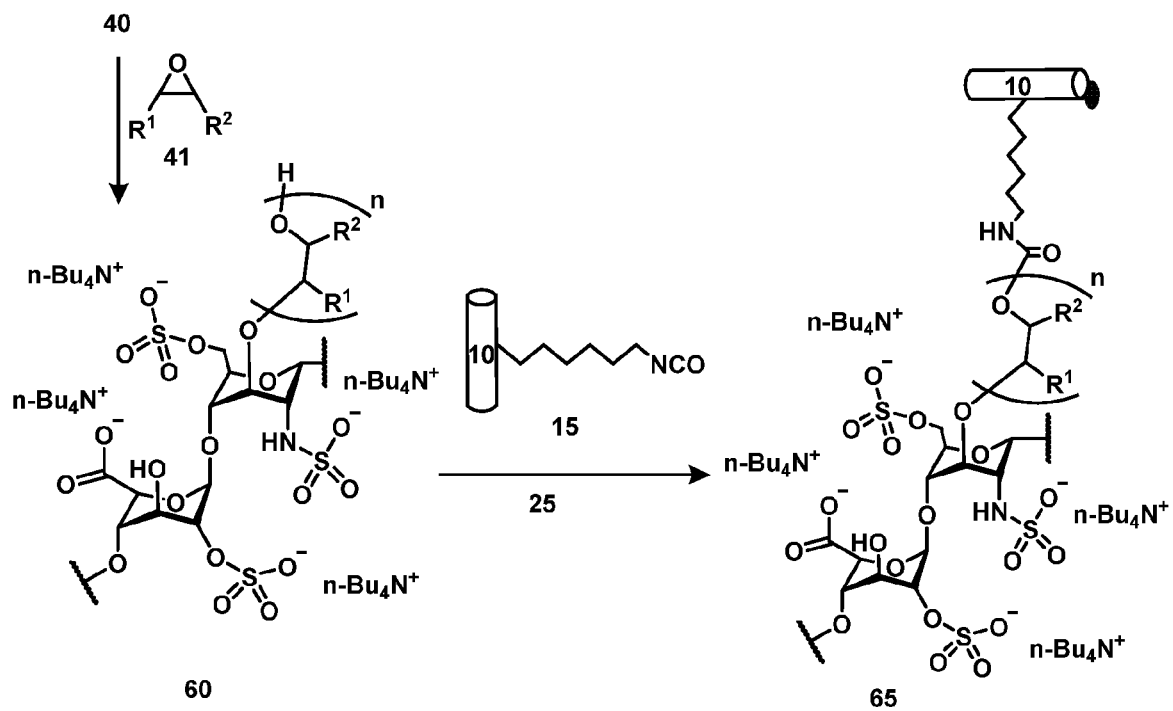
FIG. 3 depicts a schematic representation of coating heparin-O(CHR$^1$CHR$^2$O)$_n$H-TBA (60) on PHMDI- or HDI-coated PU tube (15) via the carbamate-forming reaction (25), to give the heparin-coated PU tube (65) of the current invention.

Examples of the products obtained when compounds of formula Ia are used are depicted in FIGS. 2 and 3. FIG. 2 depicts the attachment of a hydroxyl group directly on the backbone of part of a heparin molecule 40 to the isocyanate-bearing substrate 15. As will be noted, the cations that counterbalance the anions in heparin in this example are tetrabutyl ammonium ions. However, it will be appreciated that any suitable quaternary ammonium cation can be used. For example, in aspects and embodiments of the invention disclosed herein the quaternary ammonium cations may be $C_{1-30}$ alkyl quaternary ammonium ions, such as $C_{1-10}$ alkyl quaternary ammonium ions, such as tetrabutyl ammonium ions.

While it is intended that all other cations are stripped from the heparin molecule, such that only quaternary ammonium cations are present, this may not be fully achievable. Therefore, as noted above, the quaternary ammonium cations make up a substantial portion of the cations associated with heparin molecules used in the processes and products disclosed herein. When used herein, the term "substantially" is intended to refer to the situation wherein at least 80%, such as at least 90%, such as at least 95%, such as at least 99%, such as at least 99.999% of the cations are quaternary ammonium ions.

FIG. 3 depicts the situation where a linker is used to functionalise the heparin backbone and there is a hydroxyl group at the terminal of the linker, which covalently bonds to the isocyanate. This is achieved by taking a heparin molecule 40 and reacting it with a suitable epoxide 41 to generate a hydroxyl group separated from the heparin backbone, shown as 60. While only one epoxide reacting with the hydroxyl group of the backbone is necessary to provide the linker, it is possible for the ring-opening oligomerisation to occur, resulting in an oligomer derived from up to 20 epoxides 41. The resulting functionalised material 60 may be reacted with an isocyanate-functionalised substrate 15 to provide a covalently-bonded product 65. Two kinds of epoxide may be used. The first may be one in which the epoxide is in a linear alkyl chain or it may be one that is formed as part of a carbocyclic ring.

As will be appreciated, the above-mentioned embodiments of FIGS. 2 and 3 are specific examples of the reaction products of the compounds of formula Ia, where $A_1$ is:

HO— (FIG. 2); or $H(OCHR_1CH_2)_xO$—, where the terminal oxygen atom is part of the Heparin molecule; or $H(OCHR_1CHR_2)_xO$—, where $R_1$ and $R_2$, together with the atoms they are attached to, form a carbocyclic ring system having from 3 to 10 carbon atoms (FIG. 3). In embodiments of the invention, x may take any suitable value, such as from 1 to 20, from 1 to 10, or from 1 to 5.

For the avoidance of doubt, it is noted that more than one $A_1$ group may be used to form a covalent bond per heparin molecule in the compounds of formula Ia. For example, from 1 to 50 $A_1$ groups may be used to form a covalent bond to an isocyanate in the substrate per molecule of heparin.

Figure 4:
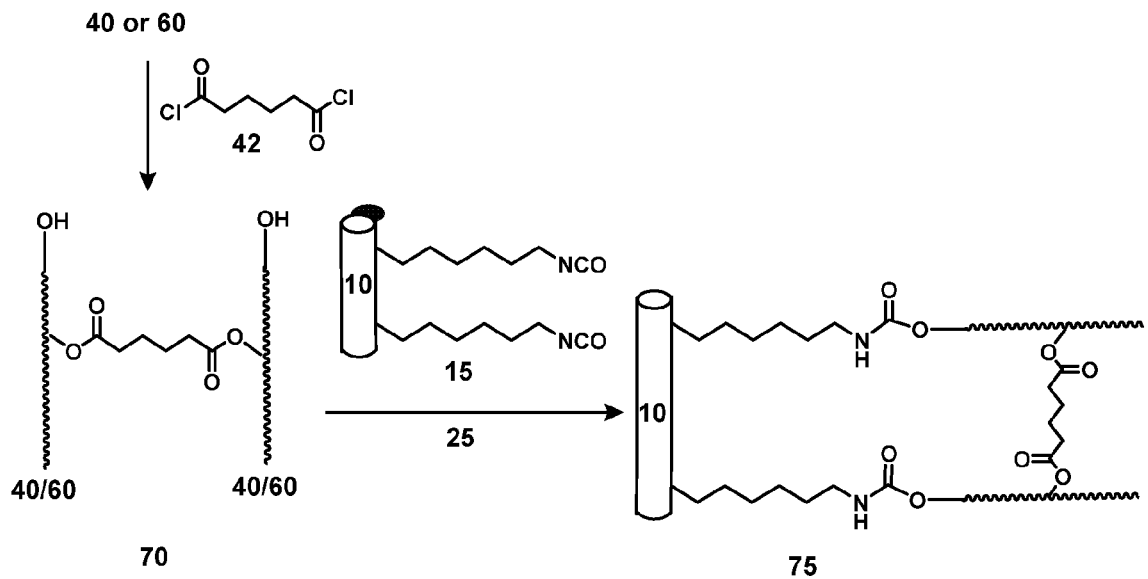
FIG. 4 depicts a schematic representation of crosslinking 40 or 60 with a linker (42) to form APC-crosslinked heparin (70), which can then be coated on PHMDI- or HDI-coated PU tube (15) via the carbamate-forming reaction (25), to give the heparin-coated PU tube (75) of the current invention.

FIG. 4 generically depicts the process of bonding a compound of formula Ib to the isocyanate-functionalised substrate. Where a linking agent 42 is first reacted to crosslink heparin chains together. The heparin chains herein can be 40 or 60. These crosslinked heparin chains may then be reacted with an isocyanate-functionalised substrate 15 to generate the desired product 75.

In compounds of formula Ib:

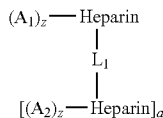

a represents 1 to 25, such as 1 to 10, such as from 2 to 5, such as from 3 to 4, representing the crosslinking of multiple heparin compounds together via crosslinking agents. For the avoidance of doubt, the crosslinking will occur in a manner that may provide a network of crosslinked heparin molecules and the formula Ib is intended to represent this network of crosslinked heparin molecules. As will be appreciated, $A_1$ and $A_2$ in the formula Ib above may take equivalent values to $A_1$ described above in relation to the compound of formula Ia. Finally, each z may independently represent from 1 to 50, representing points of attachment between each heparin molecule and the isocyanate-functionalised substrate.

In embodiments of the invention, the crosslinking moiety $L_1$ may be derived from one or more of the group consisting of a linear or branched di-acid chloride, a linear or branched tri-acid chloride, a linear or branched di-epoxide, a linear or branched tri-epoxide, and a linear or branched tetrakis-epoxide. Examples of such groups include, but are not limited to adipoyl chloride, dodececanedioyl dichloride, sebacoyl dichloride, suberoyl dichloride, 1,2-butanediol diglycidyl ether, neopentyl glycol diglycidyl ether, and trimethylolpropane triglycidyl ether.

In certain embodiments of the invention relating to the compounds of formula Ia and Ib, each $R_1$ may represent H or a $C_1$ to $C_5$ alkyl group.

Figure 5:
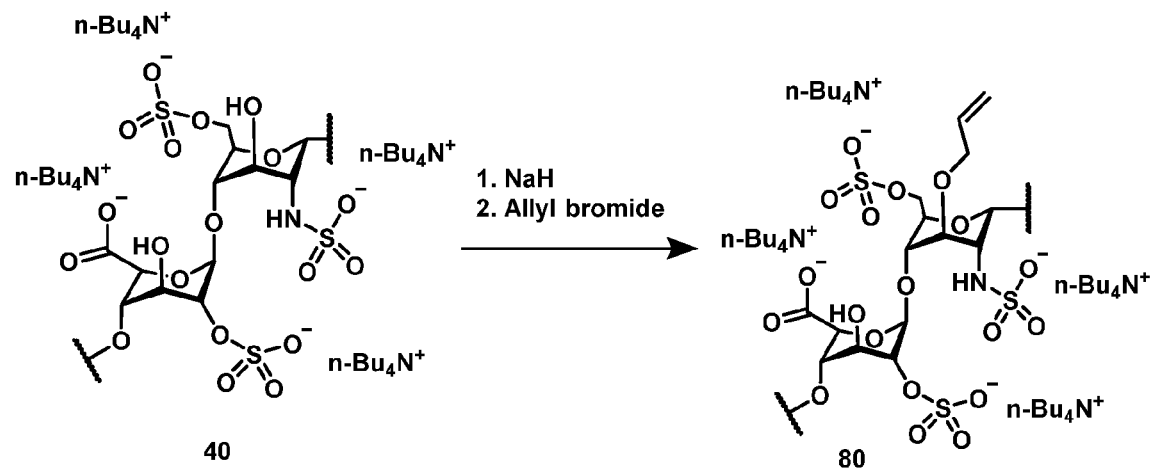
FIG. 5 depicts a schematic representation of: (a) preparing a modified heparin-TBA with alkene functionality (80); and (b) preparing a thiol-functionalised heparin-TBA (95) for coating on PHMDI- or HDI-coated PU tube (15) via the thiol-isocyanate click reaction (35), to give the heparin-coated PU tube (100) of the current invention.
Figure 5:
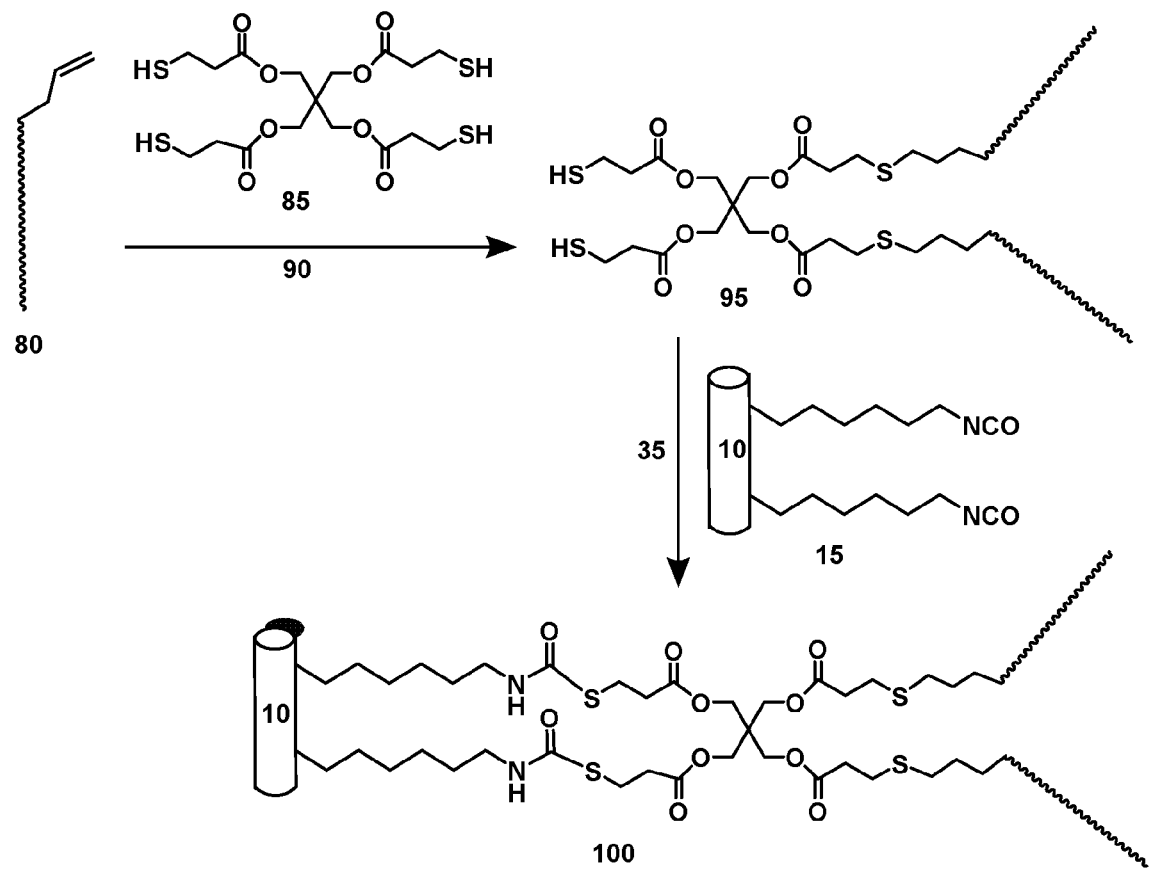
Figure 6:
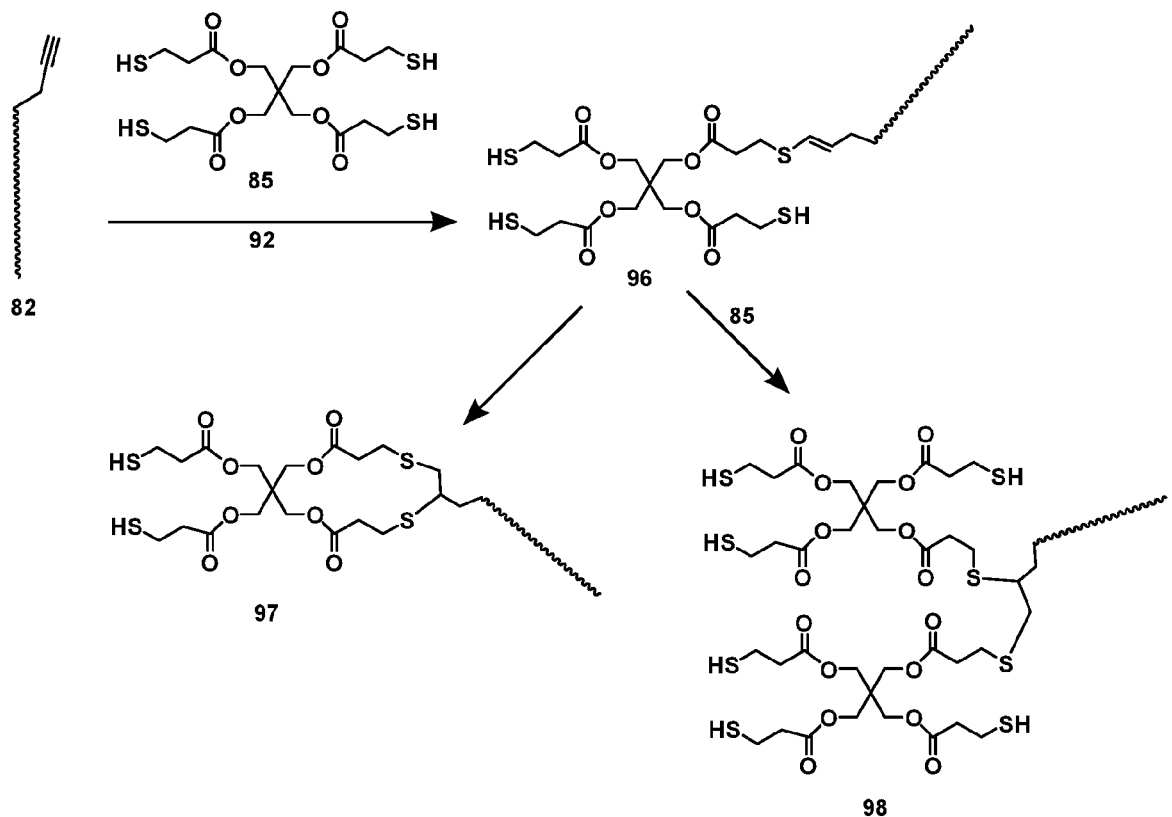
FIG. 6 depicts a schematic representation of reacting alkyne-functionalised heparin-TBA (82) with linker (85) to form thiol-functionalised heparin-TBA (97 and 98).

Examples of the products obtained by reacting an isocyanate-functionalised substrate with the compounds of formula Ic to If are depicted in FIGS. 5(b) and 6. In embodiments of the invention using such compounds, one or more of the following may apply:

(i) each n, n', n", n''' independently represent 1 to 25, such as from 2 to 10, such as from 3 to 5;

(ii) each m, m', m", p, p', p", p''' and p'''' independently represent 1 to 10, such as 1 to 3;

(iii) each q independently represents 1 to 15, such as 1 to 10, such as 1 to 6;

(iv) each $L_2$ to $L_5$ each independently represent a linking group in the form of a branched or unbranched $C_{1-10}$ alkyl chain, which alkyl chain is unsubstituted or substituted by one or more groups selected from $C_{1-6}$ alkyl, O or N, or which alkyl chain may be interrupted by a heteroatom (such as O, N); and/or (v) each o and o' independently represents 1 to 10, such as 1 to 2.

In the compounds of formula Ic-If, one or multiple thiol groups are grafted onto the heparin molecule. This is achieved by first functionalising the heparin with an alkene- or alkyne-bearing group, which may be achieved using a suitable alkylene halide (e.g. allyl bromide), as depicted in FIG. 5a. Subsequently the alkene functionalised heparin can be reacted with a compound containing at least two thiol groups in a thiol-ene click reaction to generate a thiol-functionalised heparin that can be used to participate in a covalent bond-forming reaction with the isocyanate-functionalised substrate in a thiol-isocyanate click reaction, as depicted in FIGS. 5b and 6. As shown in FIGS. 5b and 6, the compounds of formulae Ic-If can contain various different networked structures, depending on the reaction of heparin with the thiol-containing compound, which may have more than two thiol groups (e.g. 2, 3, 4, 5, 6, 7, 8 thiol groups). These multiple thiol groups may act to crosslink a number of heparin molecules together to generate a network of heparin molecules, which are then bonded to the isocyanate functionalised substrate by the free thiol groups. Further details concerning the methods of producing the medical devices disclosed above are provided below.

It is believed that compounds of formulae Ib-If, which may be formed as a network of heparin molecules may provide a product with exceptional stability even compared to the products that use the compound of formula Ia, which also provides substantial stability.

As an example, FIG. 6 depicts that the thiol groups can be introduced to an alkyne-functionalised-heparin-TBA (82) which is prepared by reacting 40 with a propargyl halide (in place of an allyl halide). As shown in FIG. 6, alkyne-functionalised heparin-TBA (82) can crosslinked by PETMP 85 via the thiol-yne click reaction in the presence of a tertiary amine catalyst (e.g. DMAP) (92). Typically, one alkynyl group on 82 reacts with two thiol groups, which may either come from: (1) a single PETMP molecule to form 97; or (2) two PETMP molecules to form 98. As will be appreciated, it is important in these reactions that the thiol groups are in molar excess over the alkynyl (or alkenyl) groups in the thiol-yne (or thiol-ene) click reaction so that the product contains free thiol groups.

Specific examples of the compounds of formula Ia to If are provided in the examples section below.

Also provided herein is a method of forming a medical device as described above, the method comprising the steps of:

(a) providing an isocyanate-bearing material on or covalently bonded to a substrate, which isocyanate-bearing material comprises one or more isocyanate groups;

(b) reacting the isocyanate-bearing material on or covalently bonded to the substrate in a polar aprotic solvent with a heparin molecule selected from one or more of the following formulae:

$(A_1)_z$—Heparin;   Ia $(A_1)_z$—Heparin
     |
     $L_1$
     |
$[(A_2)_z$—Heparin$]_a$;   Ib and Ic: $\{([HS(CH_2)_n]_m\text{-}L_2\text{-}[(CH_2)_nS(CH_2)_oO])_z\text{-}Heparin\}_p$, where the oxygen atom bonded to Heparin is part of the Heparin molecule;

Id: $\{([HS(CH_2)_{n'}]_{m'}\text{-}L_3\text{-}[(CH_2)_nS(CH_2)_oCOO])_z\text{-}Heparin\}_{p'}$, where the oxygen atom bonded to Heparin is part of the Heparin molecule;

Ie: $\{([HS(CH_2)_{n''}]_{m''}\text{-}L_4\text{-}[(CH_2)_nS(C_qH_{2q-2})O])_z\text{-}Heparin\}_{p''}$, where the oxygen atom bonded to Heparin is part of the Heparin molecule; and If: a network of heparin molecules comprising fixing portions of formula Ifi:

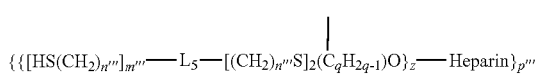

where the oxygen atom bonded to Heparin is part of the Heparin molecule; and network extending portions of formula Ifii:

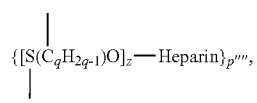

where the oxygen atom bonded to Heparin is part of the Heparin molecule;

to provide the medical device described in any one of claims 1 to 10, where:

each $A_1$ and $A_2$ independently represent:
HO—;
$H(OCHR_1CH_2)_xO$—, where the terminal oxygen atom is part of the Heparin molecule; or
$H(OCHR_1CHR_2)_x$, where $R_1$ and $R_2$, together with the atoms they are attached to, form a carbocylic ring system having from 3 to 10 carbon atoms;

$L_1$ represents a crosslinking moiety;

a represents 1 to 25;

each z independently represents 1 to 50;

each n, n', n", n''', o and o' independently represent 1 to 20;

each m, m', m", m''', p, p', p", p''' and p'''' independently represent 1 to 20;

each q independently represents 1 to 20;

each $L_2$ to $L_5$ each independently represent a linking group;

$R_1$ represents H or a $C_1$ to $C_{20}$ alkyl group;

x represents from 1 to 20;

| in formula Ib represents a covalent bond between a Heparin molecule and the crosslinking moiety;

each | in formula Ifi represents a point of attachment to a further fixing portion of formula Ifi or to an extending portion of formula Ifii;

each | in formula Ifii represents a point of attachment to a fixing portion of formula Ifi or to a further extending portion of formula Ifii;

each Heparin molecule is a polyanionic molecule, where each negative charge is balanced by a cation, wherein:
the cations are substantially quaternary ammonium ions; and
the isocyanate-bearing material is a coating on the substrate or is covalently bonded to the substrate.

As will be appreciated, the compounds of formulae Ia-If and the substrate material are the same as defined above.

The polar aprotic solvent may be any suitable polar aprotic solvent. However, when the substrate is a polymeric material, the polar aprotic solvent is preferably a material that will not solubilise or otherwise substantially degrade the selected polymer. In particular embodiments of the invention that may be mentioned herein, the polar aprotic solvent may be acetonitrile. As will be appreciated, the use of quaternary ammonium ions enables the use of polar aprotic solvents in the reactions described herein.

Compounds of formula Ia where $A_1$ is $H(OCHR_1CH_2)_xO$— or $H(OCHR_1CHR_2)_xO$— may be formed by reacting heparin with an epoxide. Compounds of formula Ib where $A_1$ and/or $A_2$ is $H(OCHR_1CH_2)_xO$— or $H(OCHR_1CHR_2)_xO$— may be formed by reacting heparin with an epoxide.

In the compounds of formula Ib, the crosslinks between the heparin molecules in the compound of formula Ib are formed by providing $(A_1)_z$-Heparin and $(A_2)_z$-Heparin, where $A_1$, $A_2$ and z are as defined above, and reacting these compounds with a crosslinking agent. The crosslinking agent may be selected from one or more of the group consisting of a linear or branched di-acid chloride, a linear or branched tri-acid chloride, a linear or branched di-epoxide, a linear or branched tri-epoxide, and a linear or branched tetrakis-epoxide. Examples of such crosslinking agents include, but are not limited to adipoyl chloride, dodececanedioyl dichloride, sebacoyl dichloride, suberoyl dichloride, 1,2-butanediol diglycidyl ether, neopentyl glycol diglycidyl ether, and trimethylolpropane triglycidyl ether.

Compounds of formula Ic-If may be prepared by reacting a heparin molecule modified to present one or more carbon to carbon double bond functional groups or carbon to carbon triple bond functional groups with a compound comprising multiple thiol groups, optionally wherein the compound comprising multiple thiol groups is selected from the group consisting of pentaerythritol tetrakis(3-mercaptopropionate), trimethylolpropane tris(3-mercaptopropionate), and 2,2'-(ethylenedioxy)diethanethiol. The heparin molecule modified to present one or more carbon to carbon double bond functional groups or carbon to carbon triple bond functional groups may be prepared by reacting heparin with:
(a) a compound of formula IIa:

where k is from 1 to 50 and XX is halo (e.g. the compound of formula IIa is allyl bromide); or
(b) a compound of formula IIb:

where k' is from 1 to 50 and XX is halo (e.g. the compound of formula IIb is propargyl bromide); or
(c) a compound of formula IIc:

where XX is halo and $R_2$ is $C_{1-50}$ alkyl (e.g. the compound of formula IIc is selected from one or more of the group consisting of 10-undecenoyl chloride, 4-pentenoyl chloride, and acryloyl chloride).

In the reactions (a) to (c) listed above, additional reactants and/or reagents may be present as required. For example, in the reactions (a) and (b) above, the heparin may be pre-treated with a based (such as NaH) before it is reacted with the compound of formula IIa or IIb. Full details of the experimental methods may be obtained from consideration of the experimental section below.

As will be appreciated, the resulting heparin-coated substrate may be useful in the treatment or prevention of conditions affecting subjects. Thus, the devices disclosed herein may be provided as a medical device:
(a) for use as heart stent or intravascular stent that is hemocompatible for preventing the formation of blood clots;
(b) for use as an organ support that is hemocompatible for preventing the formation of blood clots;
(c) for use in blood collection and separation; and
(d) for use in preventing blood clots.

These medical devices may be used in suitable methods of treatment wherein the method comprises the step of inserting the medical device into a subject in need thereof to provide the desired effect(s) noted above. As will be appreciated, at least part of these medical devices may be consumed upon use in a subject in need to treatment and to there is also provided a use of a medical device as described above in the preparation of a medicament:
(a) for use as heart stent or intravascular stent that is hemocompatible for preventing the formation of blood clots;
(b) for use as an organ support that is hemocompatible for preventing the formation of blood clots;
(c) for use in blood collection and separation; and
(d) for use in preventing blood clots.

Further aspects and embodiments of the invention are provided in the following non-limiting examples.

EXAMPLES

The current invention relates to a medical device comprising a covalently-bonded heparin coating on a substrate, which can be achieved as shown in the schematic representation of FIG. 1. An isocyanate-coated device 15 is first prepared by first coating a polyurethane (PU) medical device or tube (10) with 12 [poly(hexamethylene diisocyanate)] (PHMDI) or hexamethylene diisocyanate (HDI)). Thereafter, device 15 can be coated with modified or unmodified heparin-tetrabutylammonium (hepain-TBA) via: (a) the carbamate-forming reaction in acetonitrile (25); or (b) the thiol-isocyanate click reaction in acetonitrile (35).

For the carbamate-forming reaction (25), the coating reaction occurs between the hydroxyl groups of 20 (heparin-TBA or epoxide-functionalised heparin-TBA) with the isocyanate groups on the surface of 15. For reaction 35, the covalent reaction takes place between the thiol groups on the thiol-functionalised heparin-TBA (30) with the isocyanate groups on the surface of 15.

Materials and Methods

The materials were purchased from the sources as provided below.
Acetonitrile (Sigma-Aldrich, Anhydrous, 99.8%),
Hexane (Sigma-Aldrich, Anhydrous, 95%),
Tetrabutylammonium chloride (Sigma-Aldrich, ≥97%),
Triethylamine (Tokyo Chemical Industry CO., LTD, >99.0%),
Calcium chloride (Sigma-Aldrich, ≥97%),
Goat blood (Quad Five),
Sodium citrate dihydrate (Sigma-Aldrich, ≥99%),
Glutaraldehyde solution (Sigma-Aldrich, Grade I, 25% in water),
Poly(hexamethylene diisocyanate) (Sigma-Aldrich, viscosity 1,300-2,200 cP (25° C.)],
Hexamethylene diisocyanate (Sigma-Aldrich, ≥98%),
Adipoyl chloride (Sigma-Aldrich, 98%),
Pentaerythritol tetrakis(3-mercaptopropionate) (Sigma-Aldrich, >95%),
Allyl bromide (Sigma-Aldrich, 99%),
Sodium hydride (Strem Chemicals, 60% dispersion in mineral oil),
Sodium chloride (Sigma-Aldrich, ≥99.5%),
Heparin (Yantai Dongcheng Biochemicals CO., LTD),
4-(Dimethylamino)pyridine (Sigma-Aldrich, ≥99%),
Cyclohexene oxide (Sigma-Aldrich, 98%), and
Dialysis membrane (Spectrum Laboratories, Inc., MWCO 3,500).

Substrate is a dual lumen polyurethane catheter (or polyurethane tube). The diameter of the catheter is 2.67 mm and the surface area is 1.87 $cm^2$ per cm length of the catheter.

Moisture sensitive compounds were handled in a MBRAUN glovebox protected with argon.
Deionised (DI) water was obtained from ELGA Ultrapure Water Treatment Systems (PURELAB Option).
$^1$H NMR and $^{13}$C NMR spectra were recorded on a JEOL 500 MHz spectrometer.
SEM imaging was performed using a JEOL JSM 6700F.
Infrared (IR) spectra were recorded on a Bruker Vertex 80v vacuum FTIR spectrometers.
Note in FTIR absorption intensity: s=strong; vs=very strong; m=medium; w=weak; and vw=very weak.

General Procedure 1—Preparation of Heparin-TBA (40)

Heparin-TBA (40) was prepared in accordance to a reported method, via ion exchange between heparin sodium with tetrabutylammonium chloride (TBACl) in water (*ACS Appl. Mater. Interfaces* 2016, 8, 8376-8385).

Typically, a 50 mL flask charged with a solution of heparin sodium (1 g in 6 mL DI water) was slowly added with a solution of tetrabutylammonium chloride (TBACl, 1.6 g in 4 mL DI water) under stirring at room temperature. The obtained mixture was stirred at room temperature for 2 days to allow complete exchange of $Na^+$ ions (of heparin sodium) with TBA ions (of TBACl). The solution was then dialysed against DI water using a dialysis membrane (with a molecular weight cut-off (MWCO) of 3500) for 16 hrs to remove NaCl and excessive TBACl. The water of the solution was removed on a rotary evaporator (with a water bath of 35° C.), affording a white solid product, which was further dried in high vacuum with an oil pump at room temperature overnight.

After product was dried overnight to remove all the water, it was observed that the heparin-TBA is soluble in water, THF, dichloromethane, and acetonitrile. The good solubility of heparin-TBA in acetonitrile is particularly useful, as it allows the use of a more chemically compatible solvent for coating the heparin-TBA (40) on the polymer devices. The as-synthesised product was characterised by $^1$H, $^{13}$C NMR and FTIR spectroscopy, and is denoted as "sample 1".

$^1$H NMR (500 MHz, D$_2$O, δ=ppm): 0.94 (triple, $J_{C-H}$=7.5 Hz), 1.35 (sext, $J_{C-H}$=7.4 Hz), 1.64 (quint, $J_{C-H}$=7.9 Hz), 3.19 (triple, $J_{C-H}$=8.3 Hz), 3.62-5.44 (broad multiple). $^{13}$C NMR (125 Hz, D$_2$O, δ=ppm): 12.91, 19.19, 23.16, 58.14, 69.37 (broad), 76.00 (broad).

FTIR absorption frequencies of sample 1 (heparin-TBA pellet, cm$^{-1}$): 2959 (m), 2934 (w), 2874 (m), 1616 (s), 1464 (m), 1381 (m), 1216 (vs), 1150 (w), 1107 (w), 1012 (vs), 935 (w), 879 (s), 801 (w), 739 (s), 682 (vw), 621 (vw), 608 (vw), 576 (s), 548 (vw), 530 (vw), 487 v(w), 414 (vw).

General Procedure 2—Preparation of PHMDI-Coated Medical PU Tubes

In a glove box (protected with argon), PHMDI (1.0 g) and anhydrous acetonitrile (20 mL) were added into a 50 mL Schlenk flask, which was gently shaken for ~5 min to form a solution. Six samples of medical PU tubes (diameter 2.67 mm, 2 cm long each) were dipped into the PHMDI-acetonitrile solution. The Schlenk flask was then removed from the glove box, connected to a Schlenk line (protected with nitrogen), and heated to 60° C. (in an oil bath) for 5 hrs. During the 5-hr coating time, the Schlenk flask was gently shaken for ~1 min for every 30 min of reaction time to prevent the PU tubes from sticking to one another or from sticking to the inner surface of the Schlenk flask. After 5 hrs of incubation, the polyurethane tubes were removed and dried in an oven at 60° C. for 1 hr. The PHMDI-coated samples were denoted as "sample 2" and were characterised by FTIR spectroscopy.

FTIR absorption frequencies of original uncoated PU tube (cm$^{-1}$): 3316 (s), 2922 (s), 2851 (s), 2797 (w), 1688 (vs), 1527 (vs), 1447 (m), 1413 (vw), 1366 (m), 1319 (m), 1228 (s), 1188 (s), 1098/1081 (vs, shoulder by shoulder), 1046 (w, shoulder), 981 (w), 899 (w), 779 (m), 636 (m), 610 (s), 453 (w).

FTIR absorption frequencies of sample 2 (PHMDI-coated PU tube, cm$^{-1}$): 3307 (s, broad), 2931 (s), 2857 (m), 2263 (vs), 1766 (m), 1684 (vs), 1639 (w, shoulder), 1515 (vs), 1352 (m), 1211 (s), 1095/1081 (m, shoulder by shoulder), 1041 (w), 981 (w), 897/876 (w, shoulder by shoulder), 771 (m), 729 (w), 636 (m), 609 (s), 582 (w, shoulder).

General Procedure 3—Preparation of HDI-Coated Medical PU Tubes

In a glove box (protected with argon), HDI (1.0 g), dibutyltin dilaurate (DBTDL, 120 mg) and anhydrous hexane (20 mL) were added into a 50 mL Schlenk flask and was gently shaken for ~5 min to give a solution. Six samples of medical PU tubes (diameter ~2.67 mm, 2 cm long each) were then dipped into the HDI solution. The Schlenk flask was then taken out of the glove box, connected to a Schlenk line (protected with nitrogen), and heated to 60° C. (in an oil bath) for 2 hrs. The PU tubes were then taken out, washed with anhydrous hexane (10 mL×4) and anhydrous acetonitrile (10 mL×4), and dried under vacuum for 1 hr. The HDI-coated samples were denoted as "sample 3" and were characterised by FTIR spectroscopy.

FTIR absorption frequencies of sample 3 (HDI-coated PU tube, cm$^{-1}$): 3320 (s), 2927 (s), 2852 (s), 2797 (w), 2268 (m), 1977 (vw), 1689 (vs), 1662 (w, shoulder), 1526 (s), 1447 (m), 1365 (w), 1320 (m), 1228 (m), 1188 (m), 1099/1081 (vs, shoulder by shoulder), 1045 (m, shoulder), 982 (m), 899 (vw), 779 (m), 636 (m), 610 (s), 451 (w).

Example 1. Coating of Heparin-TBA (40) on PHMDI-Coated Polyurethane Tube (15) Via the Carbamate-Forming Reaction (25)

To prepare a heparin-coated device of the current invention (50), heparin-TBA (40) can be used directly in the carbamate-forming reaction 25 (in acetonitrile) as the hydroxyl groups of heparin can react directly with the isocyanate groups of the PHMDI-coated tube 15 (FIG. 2).

In a typical reaction, heparin-TBA 40 (500 mg) and anhydrous acetonitrile (10 mL) were added into a 50 mL Schlenk flask in a glove box (protected with argon), and was gently shaken for ~5 min to give a solution. The Schlenk flask was then taken out of the glove box, connected to a Schlenk line (protected with nitrogen), and heated to 60° C. in an oil bath.

Two freshly prepared PHMDI-coated PU tubes (prepared in accordance to general procedure 2) were dipped into the solution and kept at 60° C. for 6 hrs. During the 6 hr-coating time, the Schlenk flask was gently shaken for ~1 min for every 30 min reaction time to prevent the PU tubes from sticking to one another or from sticking to the inner surface of the Schlenk flask. After 6 hrs of incubation, the PU tubes were removed and dried in an oven at 60° C. for 2 hr. The as-synthesised heparin-TBA-coated tubes 50 were denoted as "sample 4" and characterised by FTIR spectroscopy.

FTIR absorption frequencies of sample 4 (PHMDI-coated PU tubes coated with heparin-TBA, cm$^{-1}$): 3419 (s, broad), 2962 (m), 2937 (w, shoulder), 2876 (m), 1615 (s), 1486 (w), 1464 (m), 1413 (w), 1382 (w), 1346 (vw), 1214 (vs), 1149 (w), 1109 (vw), 1053 (vw, shoulder), 1024 (vw, shoulder), 1009 (vs), 937 (w), 880 (m), 806 (m), 739 (m), 577 (m), 531 (w), 488 (w), 416 (w).

Example 2. Coating of Heparin-O(CHR$^1$CHR$^2$O)$_n$H-TBA (60) on PHMDI- or HDI-Coated Polyurethane Tube (15) Via the Carbamate-Forming Reaction (25)

Other than the use of heparin-TBA for direct coating onto the isocyanate-coated medical devices, other modified forms of heparin-TBA (40) can also be used. In an embodiment of the current invention, heparin-TBA (40) can be modified with epoxides (41), prior to coating onto PHMDI- or HDI-coated PU tube (15) via the carbamate-forming reaction (25) (FIG. 3).

The ring-opening reaction of epoxide with the hydroxyl groups of heparin-TBA allows the re-positioning of some of the hydroxyl groups further away from the heparin carbon backbone to facilitate the carbamate-forming reaction (25) with isocyanate. This means that the epoxide-modified heparin can be coated more efficiently or easily onto the PU tube than heparin-TBA.

Typically, the reaction can be carried out at elevated temperature, with or without a catalyst to promote the reaction. Examples of catalysts are triethylamine, dimethylaminopyridine (DMAP) and 1,1,3,3-tetramethylurea. The general formula of the epoxide-modified heparin (60) can be represented as heparin-O(CHR$^1$CHR$^2$O)$_n$H-TBA, wherein R$^1$ and R$^2$ represent the substituents of the epoxide and n represents the number of epoxide molecules reacted. Epoxide modified heparin-TBA (60) can be coated on PU tubes in the same way as coating heparin-TBA, as shown in FIG. 3. An example of epoxide used is cyclohexene oxide.

Coating of Heparin-O(CHR$^1$CHR$^2$O)$_n$H-TBA (60) on PHMDI-Coated Polyurethane Tube (15)

In a typical reaction, heparin-TBA (40) (1.0 g), cyclohexene oxide (256 mg) and anhydrous acetonitrile (10 mL) were added into a 50 mL Schlenk flask in a glove box (protected with argon), and was gently shaken for ~5 min to from a solution. The Schlenk flask was taken out of the glove box, connected to a Schlenk line (protected with nitrogen), and heated to 80° C. in an oil bath under stirring for 8 hrs to produce the corresponding heparin-O(CHR$^1$CHR$^2$O)$_n$-TBA (60). The reaction mixture was cooled to room temperature, before two PHMDI-coated polyurethane tubes (prepared in accordance to general procedure 2) were dipped into the solution at room temperature for 1 min. The coated tubes were then removed and then dried in an oven at 60° C. for 30 min. This coating procedure was repeated one more time, followed by drying in the oven for 1 hr. The obtained samples were denoted as "sample 5" and were characterised by FTIR spectroscopy.

FTIR absorption frequencies of sample 5 (PHMDI-coated PU tubes coated with heparin-O(CHR$^1$CHR$^2$O)$_n$H-TBA (60), cm$^{-1}$): 3402 (s, broad), 2961 (s), 2936 (w, shoulder), 2875 (m), 1620 (s), 1514 (vw), 1486 (vw, shoulder), 1461 (m), 1421 (w), 1381 (w), 1345 (vw), 1215 (vs), 1151 (w, shoulder), 1108 (vw), 1054 (vw, shoulder), 1025/1012 (vs, shoulder by shoulder), 937 (w), 882 (m), 807 (w), 761/741 (m, shoulder by shoulder), 624 (w, shoulder), 624 (vw), 606 (vw), 577 (m), 534 (vw), 425 (w).

Coating of Heparin-O(CHR$^1$CHR$^2$O)$_n$H-TBA (60) on HDI-Coated Polyurethane Tube (15)

The coating of heparin-O(CHR$^1$CHR$^2$O)$_n$H-TBA (60) on HDI-coated PU tubes was performed using the same procedure as described above [Coating of heparin-O (CHR$^1$CHR$^2$O)$_n$H-TBA (60) on PHMDI-coated polyurethane tube (15)]. The obtained samples were denoted as "sample 6" and were characterised by FTIR spectroscopy.

FTIR absorption frequencies of sample 6 (HDI-coated PU tubes coated with heparin-O(CHR$^1$CHR$^2$O)$_n$H-TBA (60), cm$^{-1}$): 3423 (s, broad), 2962 (s), 2937 (w), 2877 (m), 1684 (w, shoulder), 1658 (w, shoulder), 1617 (s), 1526 (w), 1487 (w), 1464 (w), 1412 (w), 1381 (w), 1320 (w), 1219 (vs), 1071 (vw, shoulder), 1054 (vw, shoulder), 1027/1012 (vs, shoulder by shoulder), 984 (vw, shoulder), 886 (m), 742 (w), 635 (w), 609 (s).

Example 3. Coating of APC-Crosslinked Heparin-TBA (40) or APC-Crosslinked Heparin-O(CHR$^1$CHR$^2$O)$_n$H-TBA (60) on PHMDI-Coated Polyurethane Tube (15) Via the Carbamate-Forming Reaction 25

The heparin-TBA (40) or epoxide modified heparin-O (CHR$^1$CHR$^2$O)$_n$H-TBA (60) can be further modified to form intermolecular crosslinks with its respective neighbouring heparin molecules. In a specific embodiment of the current invention, crosslinking can be achieved by reacting the hydroxyl groups of 40 or 60 with a linker 42 (i.e. adipoyl chloride (APC)), in the presence of a base (triethyl amine) to give the crosslinked product 70 (FIG. 4). Alternatively, intermolecular crosslinking can be achieved using reaction of 40 or 60 with a linker containing multiple epoxide groups. The intermolecular crosslinks increase the bonding density of heparin onto the isocyanate-coated medical devices, which reduces the leaking of heparin from the medical devices. As such, the lifetime of the obtained heparin layer on the device can be improved.

Coating of APC-Crosslinked Heparin-TBA (40) on PHMDI-Coated Polyurethane Tube (15)

In a typical reaction, heparin-TBA (40) (1.0 g) and anhydrous acetonitrile (10 mL) were added into a 50 mL Schlenk flask in a glove box (protected with argon), and was gently shaken for ~5 min to from a solution. Triethyl amine (192 mg) was then added to the solution. Under stirring, a solution of APC (120 mg in 1.5 mL ACN) was added dropwise to the solution under stirring in 5 min, and thereafter, the reaction mixture was stirred at room temperature for 30 min. Two PHMDI-coated PU tubes (prepared in accordance to general procedure 2) were dipped into the solution at room temperature for 1 min, then removed and dried in an oven at 60° C. for 10 min. The coating procedure was repeated two times, followed by drying in an oven at 60° C. for 2 hrs. The obtained samples were denoted as "sample 7" and were characterised by FTIR spectroscopy.

FTIR absorption frequencies of sample 7 (PMHDI-coated PU tubes coated with APC-crosslinked heparin-TBA (40), cm$^{-1}$): 3317 (s, broad), 2960 (s), 2935 (m), 2875 (m), 1715 (w), 1687 (w), 1660 (w), 1625 (w), 1525 (m), 1465 (m), 1381 (w), 1319 (vw), 1224 (vs), 1151 (vw), 1106 (vw, shoulder), 1055 (vw, shoulder), 1027/1013 (vs, shoulder by shoulder), 938 (w), 884 (m), 805 (w), 779 (w), 741 (w), 686 (vw), 610 (m), 577 (w), 492 (vw).

Coating of APC-Crosslinked Heparin-O(CHR$^1$CHR$^2$O)$_n$H-TBA (60) on PHMDI-Coated Polyurethane Tube (15)

The heparin-O(CHR$^1$CH R$^2$O)$_n$H-TBA (60) solution was prepared in accordance to the same procedure in Example 2. After cooling to room temperature, a solution of APC (60 mg in 1 mL ACN) was added dropwise to solution 60 under stirring in 5 min, and thereafter, the reaction mixture was stirred for 30 min at room temperature. Two PHMDI-coated PU tubes (prepared in accordance to general procedure 2) were dipped into the solution at room temperature for 1 min, then removed and dried in an oven at 60° C. for 10 min. The coating procedure was repeated two times, followed by drying in an oven at 60° C. for 2 hrs. The obtained samples were denoted as "sample 8" and were characterised by FTIR spectroscopy.

FTIR absorption frequencies of sample 8 (PMHDI-coated PU tubes coated with APC-crosslinked heparin-O (CHR$^1$CHR$^2$O)$_n$H-TBA (60), cm$^{-1}$): 3313 (s, broad), 2928 (s), 2852 (s), 2796 (w), 1689 (s), 1661 (w, shoulder), 1525 (s), 1447 (m), 1412 (vw), 1366 (w), 1320 (w), 1227 (s), 1188 (s), 1098 (w, shoulder), 1080 (vs), 1041 (m, shoulder), 982 (m), 898 (w), 808 (vw), 779 (m), 636 (m), 609 (s), 443 (w).

Example 4. Coating of PETMP Crosslinked Heparin-TBA (95) on Polyurethane Tube Via the Thiol-Isocyanate Click Reaction 35

Besides the carbamate-forming reaction 25, the isocyanate-coated device (15) can be coated with a thiol-functionalised heparin TBA (95, 97 and 98) via the thiol-isocyanate click reaction in acetonitrile (35) (FIGS. 5b and 6). The reaction takes place between thiol groups on the thiol-functionalised heparin-TBA with the isocyanate groups on the surface of 15.

In an embodiment of the invention, the thiol groups can be introduced to heparin-TBA (40) in two steps. First, heparin-TBA is introduced with carbon double bond(s) or carbon triple bond(s). In a typical procedure, heparin-TBA (40) is introduced with carbon double bonds by alkylation with NaH/allyl bromide or by reaction with acyl chloride to provide a modified heparin-TBA with alkene functionality (80) (FIG. 5*a*).

Subsequently, thiol groups are introduced by the thiol-ene click reaction (reaction between thiol groups and double bonds) or the thiol-yne click reaction (reaction between thiol groups and triple bonds). The thiol-ene click reaction involves crosslinking 80 with excess multi-thiol compounds, such as pentaerythritol tetrakis(3-mercaptopropionate) (PETMP, 85) in the presence of a tertiary amine catalyst (e.g. DMAP) (90) to give a PETMP crosslinked heparin having excess thiol groups (95) (FIG. 5*b*). The PETMP crosslinked heparin 95 is then covalently coated on the isocyanate-coated device (15) by the thiol-isocyanate click reaction (35) to give the coated tubes 100.

Coating of PETMP Cross/lnked Heparin-TBA (95) on PHMDI-Coated Polyurethane Tube (15) Via the Thiol-Isocyanate Click Reaction 35

In a glove box (protected with argon), heparin-TBA 40 (1.0 g) and anhydrous acetonitrile (10 mL) were added into a 50 mL Schlenk flask, and was gently shaken for ~5 min. to give a solution. Under stirring, a slurry of NaH (26 mg) in 2 mL anhydrous acetonitrile was added dropwise within 5 min at room temperature (gas generated), and stirring was continued for 20 min. A solution of allyl bromide (79 mg) in 2 mL anhydrous acetonitrile was then added dropwise within 5 minutes, and stirring was continued for 3 hrs. 4-Dimethylaminopyridine (DMAP, 40 mg) was added, and stirring was continued for 2 hrs. Under stirring at room temperature, the obtained solution was added dropwise to a solution of pentaerythritol tetrakis(3-mercaptopropionate) (PETMP, 160 mg; 85) in 10 mL anhydrous acetonitrile, and stirring was continued for 6 hrs, affording a solution of PETMP-crosslinked heparin-TBA bearing excessive thiol groups (95).

Two PHMDI-coated polyurethane tubes (prepared in accordance to general procedure 2) were dipped into the PETMP-crosslinked heparin-TBA solution 95 at room temperature for 1 min, then taken out to be dried in an oven at 60° C. for 30 min. This coating procedure was repeated two times, and then the tubes were dried in an oven at 60° C. for 1 hr. The obtained samples were denoted as "sample 9" and were characterised by FTIR spectroscopy.

FTIR absorption frequencies of sample 9 (PHMDI-coated PU tubes coated with PETMP crosslinked heparin-TBA, cm$^{-1}$): 3318 (s, broad), 2960 (w, shoulder), 2932 (s), 2858 (m), 2270 (w), 1683 (s), 1659 (m), 1521 (s), 1466 (m), 1348 (vw), 1217 (vs), 1097 (vw), 1074 (w), 1034 (m), 1013 (vw, shoulder), 984 (vw, shoulder), 887 (w), 805 (vw), 775 (w), 735 (vw), 635 (w), 609 (s).

Coating of PETMP Cross/lnked Heparin-TBA (95) on HDI-Coated Polyurethane Tube (15) Via the Thiol-Isocyanate Click Reaction 35

Two HDI-coated polyurethane tubes 15 prepared according to General Procedure 3 were dipped into the PETMP-crosslinked heparin-TBA solution 95 (prepared according to procedure above in the current example) for 1 min. The samples were then dried in an oven at 60° C. for 1 hr. The obtained samples were denoted as "sample 10" and were characterised by FTIR spectroscopy.

FTIR absorption frequencies of sample 10 (HDI-coated PU tubes coated with PETMP crosslinked heparin-TBA, cm$^{-1}$): 3327 (s, broad), 2962 (m), 2936 (m), 2876 (m), 1737 (m), 1687 (w), 1647 (w), 1620 (m), 1526 (m), 1487 (vw), 1465 (w), 1414 (vw), 1382 (w), 1354 (vw), 1320 (vw), 1226 (vs), 1097 (vw, shoulder), 1070 (vw, shoulder), 1029 (vs), 1014 (vw, shoulder), 886 (m), 806 (vw), 779 (m), 741 (w), 635 (w), 609 (s), 538 (vw), 465 (vw), 452 (vw), 425 (vw).

Example 5: In Vitro Blood Test of the Heparin Coated PU Tubes

The heparin coated samples 4-10, original uncoated PU tube (or "control sample" here), PHMDI-coated PU tube (from general procedure 2) and HDI-coated PU tube (from general procedure 3) were tested with goat blood for their antithrombotic effect.

Sample Preparation

The samples or PU tubes/catheters were cut into 1 cm segments. Prior to the test, the samples 4 to 10 were incubated in ultra-pure water for 24 hrs to release un-bonded heparin-TBA.

Test Procedure

The test was performed at room temperature. Each 1 cm tube segment sample was placed into a 15 mL polypropylene (PP) tube with 1 mL of goat blood. Details of the goat blood used are described in Table 1. The test set-up is described in Table 2.

TABLE 1

| Information of goat blood. | |
| --- | --- |
| Product | Donor Goat Blood/Na$_3$-Citrate |
| Description | Goat whole blood recovered from whole blood donations from normal healthy goats. |
| Citrate concentration | Volume ratio (v/v) of (4 wt % Sodium citrate solution):blood = 1:9 |

TABLE 2

| Test set-up for samples 4-10. | | | |
| --- | --- | --- | --- |
| Item/Sample name | Set | Volume of goat blood | Ratio |
| Samples 4 to 10 | Set 1: 1 pcs, 1.87 cm$^2$ | 1.0 ml | 1.87 cm$^2$ per ml |

To start the test, a volume of CaCl$_2$ aqueous solution (0.68% w/v) was added into the PP tube to achieve a molar ratio (CaCl$_2$ to Na$_3$-Citrate) of 1:4. The resulting mixture was shaken vigorously to achieve quick and homogeneous mixing. Upon addition of CaCl$_2$, the time taken for the control sample to clot was measured using a stop-watch. The time measurement was stopped when the control sample was visually observed to be coagulated. Immediately, all the coagulation tests of the samples 4-10 were terminated by taking out the samples from the blood and the samples were observed for coagulation. All samples were washed with 1×PBS and the adsorbed blood cell were fixed by immersing into 2.5% glutaraldehyde in 1×PBS overnight at 4° C. before drying. After cell fixation, all samples were flushed with water quickly and vacuum dried before the surface morphology of the samples were observed using Scanning Electron Microscopy JOEL JSM-6700.

Results

Figure 7:
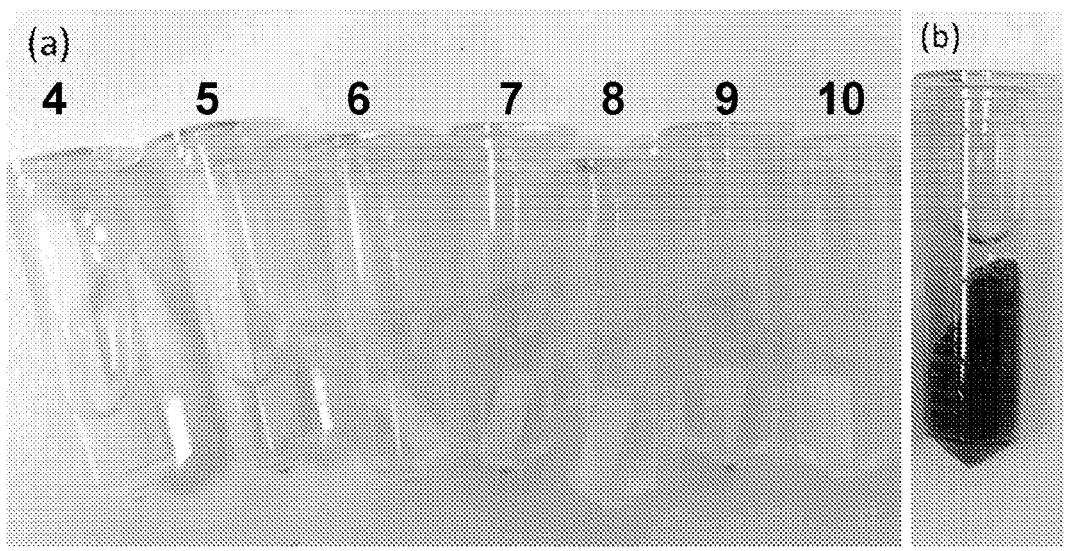
FIG. 7 depicts the photographs of: (a) samples 4-10 of the current invention after in vitro test with goat blood and dipped in DI water; and (b) an untreated PU tube (encapsulated by the blood clots) after in vitro test with goat blood and dipped in DI water.

Samples 4 to 10 all displayed antithrombogenic capability. No blood clots were observed on the surfaces of the heparin coated PU tubes (FIG. 7*a*). In contrast, a lot of blood clots were formed on the surface of original PU tube (FIG. 7b), PHMDI-coated PU tube and HDI-coated PU tube (results not provided here).

Figure 8:
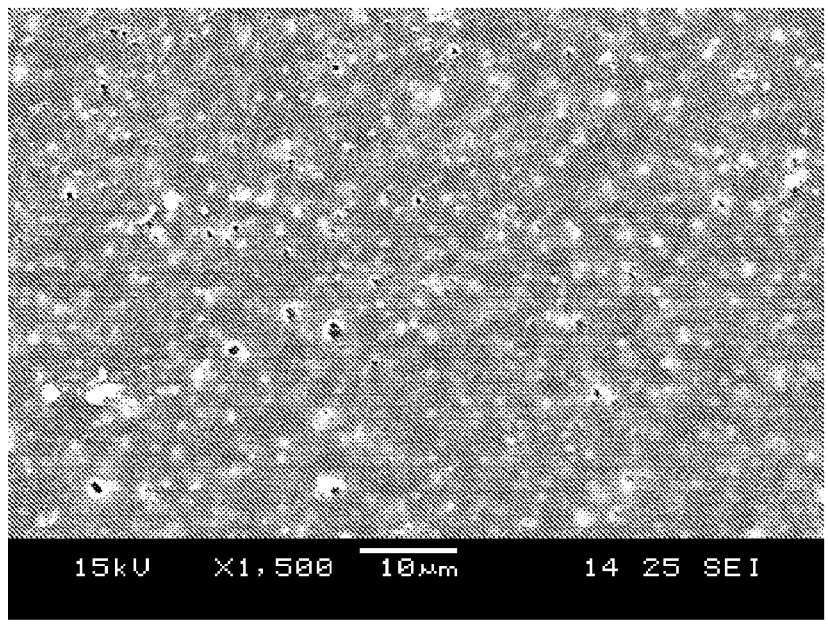
FIG. 8 depicts the SEM images of: (a) sample 5 (PHMDI-coated PU tubes coated with heparin-O(CHR$^1$CHR$^2$O)$_n$H-TBA (60)); and (b) the control sample (uncoated PU tube) after the in vitro blood test.
Figure 8:
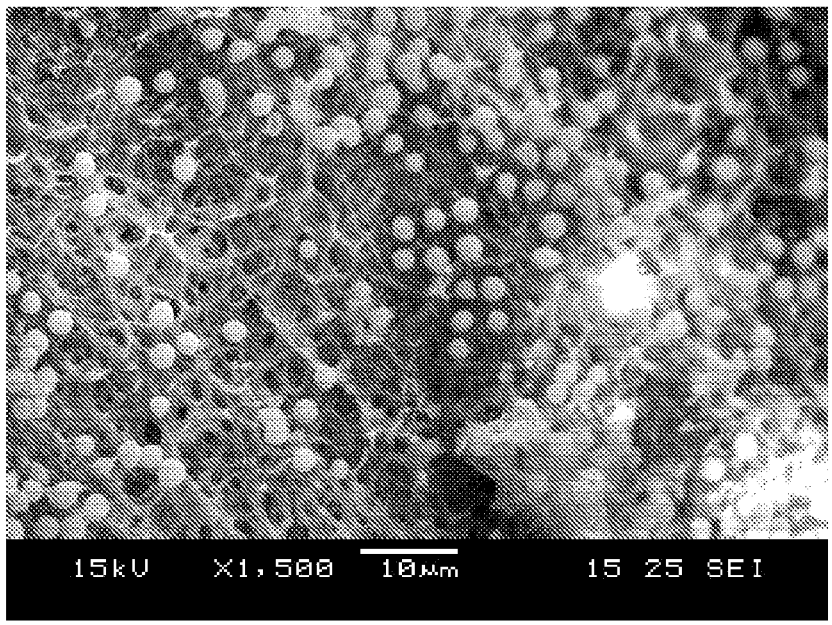

Comparing the SEM images, sample 5 (FIG. 8a) contains very little platelet adhesion as compared with the control sample (FIG. 8b). The porous surface of PU still can be clearly seen on the coated sample 5, while the surface of the control sample is covered by platelets and fibrinogen.

The invention claimed is:

1. A medical device, comprising a covalently-bonded heparin coating on a substrate, where the covalently bonded heparin coating is the reaction product of:
   (a) an isocyanate-bearing material on or covalently bonded to the substrate, which isocyanate-bearing material comprises one or more isocyanate groups; and
   (b) a heparin molecule selected from one or more of the following formulae:
   Ia: $(A_1)[[_z]]$-Heparin, where there are one or more $A_1$ groups attached to the Heparin backbone;

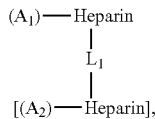

Ib where there are one or more of each of the $A_1$ and $A_2$ groups attached to the Heparin backbone; and Ic: $\{([HS(CH_2)_n]_m\text{-}L_2\text{-}[(CH_2)_nS(CH_2)_oO])[[_z]]\text{-}Heparin\}_p$, where there are one or more $([HS(CH_2)_n]_m\text{-}L_2\text{-}[(CH_2)_nS(CH_2)_oO])$— groups attached to the Heparin backbone and the oxygen atom bonded to Heparin is part of the Heparin molecule;

Id: $\{([HS(CH_2)_{n'}]_{m'}\text{-}L_3\text{-}[(CH_2)_{n'}S(CH_2)_{o'}COO])[[z]]\text{-}Heparin\}_{p'}$, where there are one or more $([HS(CH_2)_{n'}]_{m'}\text{-}L_3\text{-}[(CH_2)_{n'}S(CH_2)_{o'}COO])$— groups attached to the Heparin backbone and the terminal oxygen atom of the COO group bonded to Heparin is part of the Heparin molecule;

Ie: $\{([HS(CH_2)_{n''}]_{m''}\text{-}L_4\text{-}[(CH_2)_{n''}S(C_qH_{2q-2})O])[[_z]]\text{-}Heparin\}_{p''}$, where there are one or more $([HS(CH_2)_{n''}]_{m''}\text{-}L_4\text{-}[(CH_2)_{n''}S(C_qH_{2q-2})O])$— groups attached to the Heparin backbone and the oxygen atom bonded to Heparin is part of the Heparin molecule; and If: a network of heparin molecules comprising fixing portions of formula Ifi:

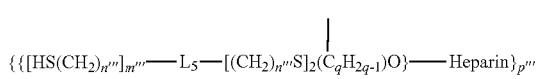

where there are one or more $\{[HS(CH_2)_{n'''}]_{m'''}\text{-}L_5\text{-}[(CH_2)_{n'''}S]_2(C_qH_{2q-1})O\}$— groups attached to the Heparin backbone and the oxygen atom bonded to Heparin is part of the Heparin molecule; and network extending portions of formula Ifii:

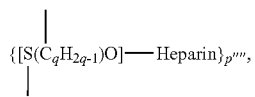

where there are one or more $[S(C_gH_{2q-1})O]$— groups attached to the Heparin backbone and the oxygen atom bonded to Heparin is part of the Heparin molecule;
where:
each $A_1$ and $A_2$ independently represent:
$HO$—;
$H(OCHR_1CH_2)_xO$—, where the terminal oxygen atom is part of the Heparin molecule; or
$H(OCHR_1CHR_2)_xO$—, where $R_1$ and $R_2$, together with the atoms they are attached to, form a carbocylic ring system having from 3 to 10 carbon atoms;
$L_1$ represents a crosslinking moiety;
each n, n', n", n''', o and o' independently represent 1 to 20;
each m, m', m", m''', p, p', p", p''' and p'''' independently represent 1 to 20;
each q independently represents 1 to 20;
each $L_2$ to $L_5$ each independently represent a linking group;
$R_1$ represents H or a $C_1$ to $C_{20}$ alkyl group;
x represents from 1 to 20;
| in formula Ib represents a covalent bond between a Heparin molecule and the crosslinking moiety;
each | in formula Ifi represents a point of attachment to a further fixing portion of formula Ifi or to an extending portion of formula Ifii;
each | in formula Ifii represents a point of attachment to a fixing portion of formula Ifi or to a further extending portion of formula Ifii;
each Heparin molecule is a polyanionic molecule, where each negative charge is balanced by a cation, wherein:
the cations are substantially quaternary ammonium ions; and
the isocyanate-bearing material is a coating on the substrate or is covalently bonded to the substrate.

2. The medical device according to claim 1, wherein in the compounds of formula Ic to If each n, n', n", n''' independently represent 1 to 25.

3. The medical device according to claim 1, wherein in the compounds of formula Ic to If, one or both of the following apply:
(a) each m, m', m", m''', p, p', p", p''' and p'''' independently represent 1 to 10; and
(b) each q independently represents 1 to 15.

4. The medical device according to claim 1, wherein in the compounds of formula Ic to If, one or both of the following apply:
(a) each $L_2$ to $L_5$ each independently represent a linking group in the form of a branched or unbranched $C_{1-10}$ alkyl chain, which alkyl chain is unsubstituted or substituted by one or more groups selected from $C_{1-6}$ alkyl, O or N, or which alkyl chain may be interrupted by a heteroatom; and
(b) each o and o' independently represents 1 to 10.

5. The medical device according to claim 1, wherein in the compounds of formula Ia and Ib, each $R_1$ represents H or a $C_1$ to $C_5$ alkyl group.

6. The medical device according to claim 1, wherein in the compound of formula Ib, one or both of the following apply:
(a) $L_1$ is a crosslinking moiety derived from one or more of the group consisting of a linear or branched di-acid chloride, a linear or branched tri-acid chloride, a linear or branched di-epoxide, a linear or branched tri-epoxide, and a linear or branched tetrakis-epoxide; and
(b) x represents 1 to 10.

7. The medical device according to claim 1, wherein the cations are substantially $C_{1-30}$ alkyl quaternary ammonium ions.

8. The medical device according to claim 1, wherein the isocyanate-bearing material is covalently bonded to the substrate.

9. The medical device according to claim 1, wherein the substrate is a polymer, a ceramic or a metal.

10. A method of forming a medical device as described in claim 1, the method comprising the steps of:
(a) providing an isocyanate-bearing material on or covalently bonded to a substrate, which isocyanate-bearing material comprises one or more isocyanate groups;
(b) reacting the isocyanate-bearing material on or covalently bonded to the substrate in a polar aprotic solvent with a heparin molecule selected from one or more of the following formulae:
Ia: $(A_1)[[_z]]$-Heparin, where there are one or more $A_1$ groups attached to the Heparin backbone;

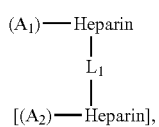

Ib where there are one or more of each of the $A_1$ and $A_2$ groups attached to the Heparin backbone; and Ic: $\{([HS(CH_2)_n]_m\text{-}L_2\text{-}[(CH_2)_nS(CH_2)_oO])[[_z]]\text{-}Heparin\}_p$, where there are one or more $([HS(CH_2)_n]_m\text{-}L_2\text{-}[(CH_2)_nS(CH_2)_oO])$— groups attached to the Heparin backbone and the oxygen atom bonded to Heparin is part of the Heparin molecule;

Id: $\{([HS(CH_2)_{n'}]_{m'}\text{-}L_3\text{-}[(CH_2)_nS(CH_2)_oCOO])[[_z]]\text{-}Heparin\}_{p'}$, where there are one or more $([HS(CH_2)_{n'}]_{m'}\text{-}L_3\text{-}[(CH_2)_nS(CH_2)_oCOO])$— groups attached to the Heparin backbone and the terminal oxygen atom of the COO group bonded to Heparin is part of the Heparin molecule;

Ie: $\{([HS(CH_2)_{n''}]_{m''}\text{-}L_4\text{-}[(CH_2)_{n'}S(C_qH_{2q-2})O])[[_z]]\text{-}Heparin\}_{p''}$, where there are one or more $([HS(CH_2)_{n''}]_{m''}\text{-}L_4\text{-}[(CH_2)_{n'}S(C_qH_{2q-2})O])$— groups attached to the Heparin backbone and the oxygen atom bonded to Heparin is part of the Heparin molecule; and If: a network of heparin molecules comprising fixing portions of formula Ifi:

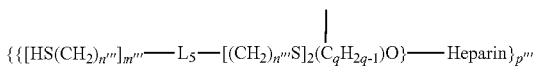

where there are one or more $\{[HS(CH_2)_{n'''}]_{m'''}\text{-}L_5\text{-}[(CH_2)_{n'''}S]_2(C_qH_{2q-1})O\}$— groups attached to the Heparin backbone and the oxygen atom bonded to Heparin is part of the Heparin molecule; and network extending portions of formula Ifii:

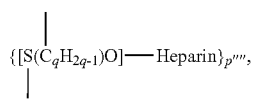

where there are one or more $[S(C_qH_{2q-1})O]$— groups attached to the Heparin backbone and the oxygen atom bonded to Heparin is part of the Heparin molecule;

to provide the medical device described in any one of claims 1 to 9, where:

each $A_1$ and $A_2$ independently represent:

HO—;

$H(OCHR_1CH_2)_xO$—, where the terminal oxygen atom is part of the Heparin molecule; or $H(OCHR_1CHR_2)_xO$—, where $R_1$ and $R_2$, together with the atoms they are attached to, form a carbocylic ring system having from 3 to 10 carbon atoms;

$L_1$ represents a crosslinking moiety;

each n, n', n'', n''', o and o' independently represent 1 to 20;

each m, m', m'', m''', p, p', p'', p''' and p'''' independently represent 1 to 20;

each q independently represents 1 to 20;

each $L_2$ to $L_5$ each independently represent a linking group;

$R_1$ represents H or a $C_1$ to $C_{20}$ alkyl group;

x represents from 1 to 20;

| in formula Ib represents a covalent bond between a Heparin molecule and the crosslinking moiety;

each | in formula Ifi represents a point of attachment to a further fixing portion of formula Ifi or to an extending portion of formula Ifii;

each | in formula Ifii represents a point of attachment to a fixing portion of formula Ifi or to a further extending portion of formula Ifii;

each Heparin molecule is a polyanionic molecule, where each negative charge is balanced by a cation, wherein:

the cations are substantially quaternary ammonium ions; and the isocyanate-bearing material is a coating on the substrate or is covalently bonded to the substrate.

11. The method according to claim 10, wherein the cations are substantially $C_{1\text{-}30}$ alkyl quaternary ammonium ions.

12. The method according to claim 10, wherein the isocyanate-bearing material is covalently bonded to the substrate.

13. The method according to claim 10, wherein when $A_1$ in the compound of formula Ia or $A_1$ and/or $A_2$ in the compound of formula Ib is $H(OCHR_1CH_2)_xO$— or $H(OCHR_1CHR_2)_xO$—, the compound of formula Ia or Ib is formed by reacting heparin with an epoxide.

14. The method according to claim 10, wherein the crosslinks between the heparin molecules in the compound of formula Ib are formed by providing $(A_1)[[_z]]$-Heparin and $(A_2)[[_z]]$-Heparin, where $A_1$, and $A_2$ are as defined in claim 10, and reacting these compounds with a crosslinking agent.

15. The method according to claim 10, wherein the compound of formula If is prepared by reacting a heparin molecule modified to present one or more carbon to carbon double bond functional groups or carbon to carbon triple bond functional groups with a compound comprising multiple thiol groups.

16. A medical device as described in claim 1 for use as heart stent or intravascular stent that is hemocompatible for preventing the formation of blood clots.

17. A medical device as described in claim 1 for use as organ support that is hemocompatible for preventing the formation of blood clots.

18. A medical device as described in claim 1 for use in blood collection and separation.

19. A medical device as described in claim 1 for use in preventing blood clots.

* * * * *